United States Patent
Pretorius

(10) Patent No.: US 8,697,149 B2
(45) Date of Patent: Apr. 15, 2014

(54) EXTRACTS AND COMPOUNDS FROM "TULBAGHIA VIOLACEA" AND THEIR USE AS BIOLOGICAL PLANT PROTECTING AGENTS

(75) Inventor: Johannes Christiaan Pretorius, Sooth (ZA)

(73) Assignees: Agrarforum AG, Bomlitz (DE); Agrarforum SA (Pty) Ltd., Bloemfontein (ZA)

( * ) Notice: Subject to any disclaimer, the term of this patent is extended or adjusted under 35 U.S.C. 154(b) by 1294 days.

(21) Appl. No.: 11/993,132

(22) PCT Filed: Jun. 24, 2006

(86) PCT No.: PCT/EP2006/006106
§ 371 (c)(1), (2), (4) Date: Dec. 19, 2007

(87) PCT Pub. No.: WO2007/003287
PCT Pub. Date: Jan. 11, 2007

(65) Prior Publication Data
US 2009/0275472 A1    Nov. 5, 2009

(30) Foreign Application Priority Data
Jun. 30, 2005 (EP) .................................. 05014247
Jun. 30, 2005 (EP) .................................. 05014265

(51) Int. Cl.
*A61K 36/8962* (2006.01)
(52) U.S. Cl.
USPC ........... 424/754; 424/778; 424/725; 424/774; 424/779
(58) Field of Classification Search
USPC ................................................ 424/725, 778
See application file for complete search history.

(56) References Cited

FOREIGN PATENT DOCUMENTS

WO    WO 98/37891    *    9/1998

OTHER PUBLICATIONS

Duncan et al. Journal of Ethnopharmacology 68 (Published 1999) 63-70.*
Kubota et al. (Biosci. Biotech. Biochem., 58 (4), p. 644-646, Published 1994).*
Duncan et al. (Journal of Ethnopharmacology, 68, p. 63-70, published 1999).*
Burton et al. (Planta Medica, 58, pp. 295-296, published 1992).*
Amusa et al. (Acta Fytotechnica et zootechnica, vol. 7, pp. 7-10, published 2004).*
Amadioha (Crop Protection, 19, Published 2000, pp. 287-290).*
Padmavati et al. (Phytochemistry, vol. 46, No. 3, Published 1997, pp. 499-502).*
Bates-Smith (The Journal of the Linnean Society (Botany) vol. 60, pp. 325-256).*
Sladkovsky et al. (Journal of Pharmaceutical and Biomedical Analysis, 24, Published 2001, pp. 1049-1054).*

* cited by examiner

*Primary Examiner* — Richard Schnizer
*Assistant Examiner* — Alma Pipic
(74) *Attorney, Agent, or Firm* — The Law Office of Ronald J Kamis

(57) ABSTRACT

The invention provides extracts and preparations based on the species *Tulbaghia violacea* (Harv.) (wild garlic), which elicits a significant antimicrobial, preferably antifungal activity in vitro and in vivo, even under field and glasshouse conditions. Moreover, these extracts deriving from the soil parts as well as of the aerial parts of the plant elicit a significant bio-stimulatory activity, expressed, above all, by an increased growth metabolism supporting seed growth. Furthermore, combined extracts or preparations from *Tulbaghia violacea* and species of the genus *Agapanthus* show a higher antifungal and bio-stimulatory efficacy as compared to the extracts or preparations of the single species, indicating that synergism is participated in the involved biological processes.

10 Claims, 6 Drawing Sheets

Figure 1:
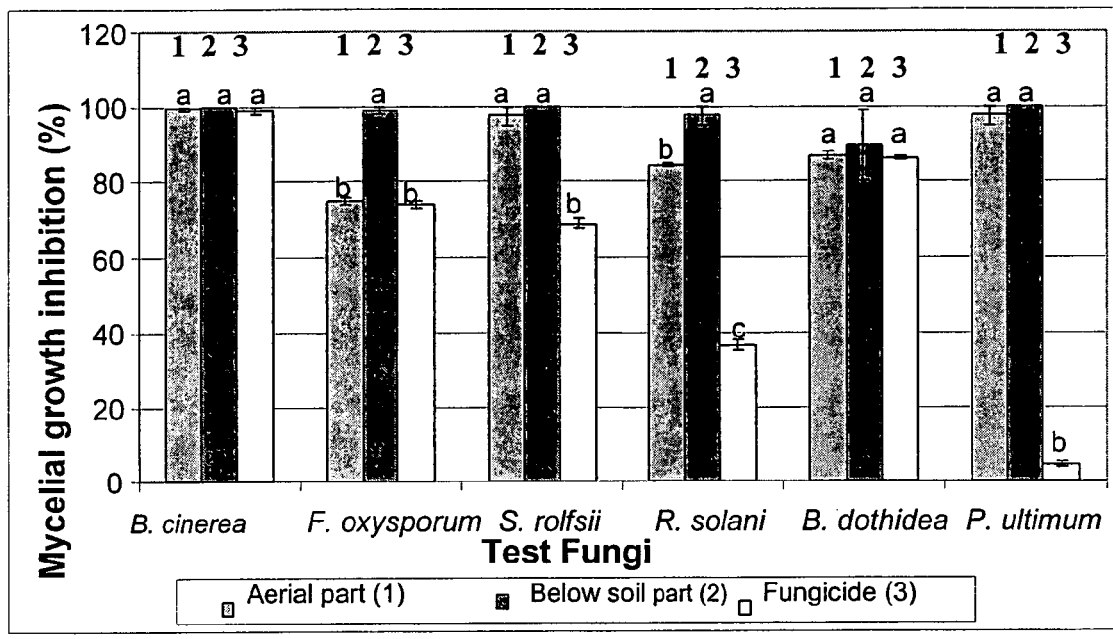

EXTRACTS AND COMPOUNDS FROM "TULBAGHIA VIOLACEA" AND THEIR USE AS BIOLOGICAL PLANT PROTECTING AGENTS

TECHNICAL FIELD OF THE INVENTION

The invention relates to plant extracts, especially based on the species *Tulbaghia violacea* (wild garlic) and combinations thereof with other extracts deriving from other plants. The invention further relates to the isolation, purification and identification of compounds in these extracts. The plant extracts and the isolated substances show significant antimicrobial activity, especially antifungal activity, and bio-stimulatory efficacy, when applied to other plants in vitro and in vivo, including under field conditions. The products according to this invention are suitable to be used as plant protecting agents for many crops and economic plants as an alternative for chemical pesticides.

BACKGROUND OF THE INVENTION

Worldwide agriculture suffers, especially in developing countries such as in Africa, from annual huge losses of crop and other economic plants due to plant diseases. More than 30% of the food, fiber, feed and energy produced in crop production systems are destroyed by insects and diseases annually on a global scale. These yield losses are high as a result of low-input production systems due to the non-affordability of synthetic fungicides to farmers in developing countries that depend on non-conventional disease management practices often providing doubtful results.

In contrast, crop and plant producers in developed countries rely largely on synthetic pesticides to control plant diseases. It is an established fact that the use of synthetic chemical pesticides provides many benefits to crop producers. These benefits include higher crop yields, improved crop quality and increased food production for an ever increasing world population.

The development of a wide range of chemicals with different formulations has enabled man to control a wide range of plant pathogens and substantially increased crop yields. More than a decade ago crop producers spent nearly $20 billion on pesticides and $150 million on other plant protection techniques, worldwide, to control pests in general. The world market share of fungicides alone was 20% in recent years whilst Europe accounted for 30% of the market. However, the same level of pathogen control has not been realized in developing countries, partly as a result of pesticide technology not being accessible to most resource poor farmers. Failure of modern approaches, technology and chemicals to reach farmers in developing countries is solely the result of high costs in relation to the value of the crops cultivated by these farmers. Consequently, crops are routinely subjected to attack from a wide spectrum of a diversity of pathogens and these farmers constantly experience serious crop damage. Moreover, yield losses are on the increase despite high pesticide usage, even in developed countries. Furthermore, control of plant diseases is not easily achieved with a single application of fungicide but requires frequent applications during the crop-growing period. However, synthetic pesticides may pose a couple of threats and hazards to the environment, especially when improperly used by farmers in developing countries who lack the technical skill of handling them, and who fail to adopt to this technology easily. This may result in undesirable residues left in food, water and the environment, and may cause toxicity to humans and animals, contamination of soils and groundwater and may lead to the development of crop pest populations that are resistant to treatment with agrochemicals. Especially sulfur and copper containing synthetic fungicides are toxic to mammals, wildlife and many beneficial insects.

Furthermore, in Africa and the Near East, obsolete pesticides have become a source of an additional great environmental concern. Some stocks are over 30 years old and are kept in poor conditions because of inadequate storage facilities and lack of staff trained in storage management. Obsolete pesticide stocks are potential time bombs. Leakage, seepage and various accidents related to pesticides are quite common and widespread.

Additionally, that frequent application of fungicides has resulted in fungal mutation and, subsequently new resistant strains (Khun, 1989, *Pesticide Science* 14:272-293), the combat of which usually requires stronger pesticides with again stronger impacts on the environment. For all these reasons there is a considerable and increasing consumer resistance especially in the developed countries, initiated politically by the green parties, towards the use of synthetic chemicals/pesticides especially, supplying a rationale for a shift from chemical pesticides applications to the use of naturally derived plant protecting agents in order to reduce the pollution and health risk caused by pesticides.

As a result, research on the possible utilization of biological resources and its application potential in agriculture has become very relevant. A promising approach in this regard is the use of natural plant products as an interesting alternative to synthetic chemicals due to the apparent less negative impact on the environment.

This especially applies to the search for environmentally friendly bioactive naturally derived components and agents with, for example, broad-spectrum antimicrobial activity.

Natural products from plants are expected to have a narrow target range and highly-specific mode of action, to show limited field persistence, to have a shorter shelf life and present no residual threats. They are generally safer to humans and the environment than conventional synthetic chemical pesticides and can easily be adopted by farmers in developing countries who traditionally use plant extracts for the treatment of human diseases.

A further rationale for exploring the use of plant extracts or natural products as biological pesticides more extensively can be found in the plant itself. Plants have evolved highly specific chemical compounds that provide defense mechanisms against attack by disease causing organisms, including fungal attack, microbial invasion and viral infection (Cowan, 1999, *Clinical Microbiology Reviews* 12:564-582). These bioactive substances occur in plants as secondary metabolites, and have provided a rich source of biologically active compounds that may be used as novel crop-protecting agents. In nature some plants have the potential to survive very harsh environmental conditions. This has initiated the postulate that such plants might be utilized as sources for the development of natural products to be applied in agriculture by man as natural herbicides, bactericides, fungicides or products in crude or semi-purified form. Secondary plant metabolites are distinct from primary metabolites in that they are generally non-essential for the basic metabolic processes such as respiration and photosynthesis. They are numerous and widespread, especially in higher plants and often present in small quantities (1-5%) as compared to primary metabolites (carbohydrates, proteins, lipids). Secondary metabolites are probably produced when required in the plant system and are synthesized in specialized cell types. Ecologically, secondary metabolites play essential roles in attracting pollinators, as adaptations to environmental stresses and serve as chemical defenses against insects and higher predators, micro-organisms and even other plants (allelochemicals). Abiotic stress such as nutrient limitation, light intensity, water stress and others has been considered to trigger the formation of secondary metabolites. A biotic stress related type of plant-pathogen interaction involves the production of metabolites as part of a plant defense arsenal against microbial invasion and is considered disease determinants. Secondary metabolites with anti-microbial properties include terpenoids (e.g. iridoids, sesquiterpenoids, saponins), nitrogen- and/or sulphur containing (e.g. alkaloids, amines, amides), aliphatics (especially long-chain alkanes and fatty acids) and aromatics (e.g. phenolics, flavonoids, bi-benzyls, xanthones and benzoquinones).

Another related area of organic farming systems is the potential to apply natural plant extracts as either plant growth regulators or bio-stimulants. Many natural plant compounds have been identified that affect the growth and development of plants. Secondary metabolites from plants may show also bio-stimulatory activities in plants, other plants included. Probably the most effective compound to enhance crop yield, crop efficiency and seed vigour has been identified as a brassinosteroid (Mandava, 1988, *Plant Physiology Plant Molecular Biology* 39:23-52). Brassionosteroids have also been identified as bio-stimulatory substances from a plant extract mixture deriving from a specific Pink species and a specific Alfalfa species (EP 1 051 075 51). An elevated interest therefore exists to identify natural plant compounds with the ability to manipulate plant growth and development over a short period, e.g. a growing season.

An additional consideration is that plants whose extracts, for example show antimicrobial and/or bio-stimulatory properties, could be cultivated as alternative agricultural crops for serving as sources of active compounds in the production of natural pesticides or plant growth regulators.

Although plants are a valuable source for the development of new natural products with the potential to be used for disease management in organic crop production systems only a small number of plants has been investigated for possible use in plant disease control in agriculture. However, related to this relatively small number of investigated plants a relatively large number of scientific research activities has been done during the last couple of years. Some of them are listed as follows:

It was shown (Pretorius et al., 2002, *Annals of Applied Biology* 141:117-124) that mycelial growth inhibition was obtained with extracts from two species of the subclass Liliidae, namely *Aristea ecklonii* and *Agapanthus inapertus*. The crude extract of *A. ecklonii* performed best of all extracts as it totally inhibited the mycelial growth of all seven of the plant pathogenic test organisms and outperformed the inhibition by a broad spectrum synthetic fungicide (carbendazim/difenoconazole). Crude extracts of *A. inapertus* showed complete inhibition of four and strong inhibition of the remaining three plant pathogenic fungi.

Plant seeds also contain compounds with antimicrobial properties. Seed extracts of 50 plant species, belonging to different families, were evaluated for their ability to inhibit the growth of *Trichoderma viride* in vitro (Bharathimatha et al., 2002, *Acta Phytopathologica et Entomologica Hungarica* 37:75-82). Of the various seed extracts, that of *Harpullia cupanioides* (Roxb.), belonging to the family Sapindaceae, displayed very high antifungal activity.

The natural plant product Milsana®, extracted from the giant knotweed (*Reynoutria sacchalinensis*), is probably best known (Daayf, 1995, *Plant Disease* 79:577-580). The product has been reported to control powdery mildew, caused by *Sphaerotheca fuliginea*, in long English cucumber under greenhouse conditions and also showed broad spectrum activity against powdery mildew of tomato, apple and begonia as well as downy mildew of grapevine and rust of bean.

Amadioha (2002, *Archives of Phytopathology and Plant Protection* 35:37-42) evaluated the antifungal activities of the different extracts of *A. indica*. The oil extract from seeds as well as water and ethanol leaf extracts of the plant were effective in reducing the radial growth of *Cochliobolus miyabeanus* in culture and in controlling the spread of brown spot disease in rice.

Kishore et al. (2002, *International Arachis Newsletter* 22:46-48) reported on the antimicrobial activity of aqueous leaf extracts from *Lawsonia inermis* and *Datura metel* against *Mycosphaerella berkeleyi* causing late leaf spot in groundnuts (*Arachis hypogaea*).

A study directed towards identifying bio-stimulatory properties in plant extracts was performed by Cruz et al. (2002, *Acta Horticulturae* 569:235-238) by treating the roots of bean, maize and tomato with an aqueous leachate of *Callicarpa acuminate*. The aqueous extract of *C. acuminata* inhibited the radical growth of tomato but had no effect on root growth of maize or beans.

Extracts from some lucerne cultivars had a stimulatory effect in terms of seed germination as well as root and hypocotyl growth, whereas others showed the direct opposite effect, confirming that crop plants can also be affected by plant extracts aimed at controlling weed growth (Tran and Tsuzuki, 2002 *Journal of Agronomy and Crop Science* 188:2-7).

Leksomboon et al. (2001, *Kasetsart Journal, Natural Sciences* 35:392-396) demonstrated the antibacterial effect of leaf and other aqueous extracts of *Hibiscus sabdariffa*, *Psidium guajava*, *Punica granatum*, *Spondias pinnata* and *Tamarindus indica* against *Xanthomonas axonopodis*, the casual agent of citrus canker under both laboratory and field conditions.

The antibacterial effects of 45 medicinal plants were evaluated against a wide range of bacteria by Morais et al. (2002 *Acta Horticulturae* 569:87-90.). Crude extracts from five of these plants significantly inhibited the growth of *Xanthomonas campestris* pv. *vesicatoria [X vesicatoria]*, *Ralstonia solanacearum* and *Clavibacter michiganense* subsp. *michiganense [C. michiganensis* subsp. *michiganensis]*, all being pathogens of tomato.

Another natural product, carvone, derived from dill and caraway seed, has been developed to inhibit the growth of storage pathogens and to suppress sprouting of potatoes in the warehouse (Moezelaar et al., 1999, *In: Modern fungicides and antifungal compounds II, Intercept Limited*, p. 453-467). Carvone is currently marketed as Talent® in the Netherlands.

In European patent EP 1 051 075 a preparation of a combination of species of the Pink family and species of Alfalfa is described (ComCat®) which reveals within a specific ratio a synergistic bio-stimulatory effect. ComCat® has demonstrated consistent plant growth enhancement and physiological efficiency in the treated plant's utilization of available nutrients. ComCat®, which enhances the health of vegetables, flowers and agricultural crops, is not a fertilizer substitute but, instead, it is a biological enhancer which stimulates the plant to more properly utilize available nutrients. Moreover, it activates and induces allelopathy and disease resistance in the treated plant and stimulates greater production of sugars, which are the building blocks for cellulose and fruiting bodies. The result is a more productive, healthier plant with stronger plant stalks, better flowering and greater fruit biomass (Agraforum: Germany, 2002, *Technical data sheet*).

SUMMARY OF THE INVENTION

The invention provides extracts and preparations based on the species *Tulbaghia violacea* (Harv.) (wild garlic), which elicits a significant antimicrobial, preferably antifungal activity in vitro and in vivo, even under field and glasshouse conditions. Moreover, these extracts deriving from the soil parts as well as of the aerial parts of the plant elicit a significant bio-stimulatory activity, expressed, above all, by an increased growth metabolism supporting seed growth. Furthermore, combined extracts or preparations from *Tulbaghia violacea* and species of the genus *Agapanthus* show a higher antifungal and bio-stimulatory efficacy as compared to the extracts or preparations of the single species, indicating that synergism is participated in the involved biological processes.

The invention provides, in addition, compositions of combinations of extracts or preparations of different plant species. These combinations comprise preparations from *Tulbaghia violacea* (wild garlic) and other plant species, such as species of the genus *Agapanthus*, preferably *A. africanus*. In the preferred combination *T. violacea* and species of *Agapanthus*, preferably *A. africanus* are mixed 1:1 (w/w). Alternatively, according to the invention, a preparation from species of *T. violacea* is combined with a preparation of a mixture of species of the Pink family and Alfalfa species, preferably in a specific ratio. In another embodiment of the invention provides combinations of species *T. violacea* with species of the genus *Agapanthus* and a mixture of species of the Pink family and Alfalfa species. These combinations elicit an increased and synergistic plant protective activity, preferably an antifungal and bio-stimulatory activity, as compared to the corresponding single-component preparations. The invention provides finally compounds isolated and purified from said extracts/preparations, which also show significant plant protecting activity, especially antifungal activity, when applied to other plants in vitro and in vivo, field cultivation included.

The preparations according to the invention can be provided as crude extracts or as dried powder dependent on the process of their manufacture. The preparations may comprise additionally, especially for use in field cultivation, solid preferably pulverulent fillers or carrier materials according to the state of the art. Moreover, the preparations according to the invention may comprise conventional additives that augment or modulate the effect of the preparation.

The preparations according to the invention can be provided also in a liquid, preferably aqueous form, which can be uses as a spray, and thus can be easily atomized on the areas under cultivation. In such solutions or suspensions the extracts and preparations of the invention reveal their full plant protecting activity in a concentration range between 0.2 g (extract/powder)/l to 2 g/l, preferably from 0.5 g/l to 1 g/l. With respect to the antifungal activity of the preparations, the term "full plant protecting activity" means 100% inhibition of the mycelial growth of a typical fungal plant pathogen compared to a standard reference pesticide.

The invention also provides processes for the manufacture of the crude extracts and dry powder preparation based on extraction of the plants or plant parts with organic polar solvents, such as methanol or ethanol or mixtures thereof. The invention finally provides a process of isolating, purifying and identifying substances from said extracts which show significant antifungal and bio-stimulatory activity in diseased plants in vitro and in vivo.

In more detail the invention provides:

A preparation suitable for biological plant protection based on plants or parts of plants from *Tulbaghia violacea* (wild garlic) in form of a crude extract, obtainable by the following steps:
  (i) drying the plant material at 30-40° C. to the exclusion of sun light;
  (ii) grinding the dried plant material to a grit size between 0.2-2 mm;
  (iii) soaking the ground material in a polar organic solvent selected from the group consisting of methanol and ethanol, thus forming a suspension/solution
  (iv) performing a stirred extraction of the suspension and separating the supernatant from the solid phase;
  (v) repeating step (iii) and (iv) at least one additional time;
  (vi) combining the soluble organic phases of step (iv) and removing the organic solvent by vacuum evaporation at 30-40° C., thus obtaining the crude extract residue.

A preparation suitable for biological plant protection based on plants or parts of plants from *Tulbaghia violacea* (wild garlic) in form of a dry powder, obtainable by the following steps:
  (i) drying the plant material at 30-40° C. to the exclusion of sun light;
  (ii) grinding the dried plant material to a grit size less than 0.1 mm,
  (iii) soaking the ground material in methanol, thus forming a suspension/solution;
  (iv) performing a stirred extraction of the suspension;
  (v) evaporating the solvent without prior separation of the solid phase from the soluble organic phase;
  (vi) soaking the evaporated solid phase residue in ethanol and repeating steps (iv) and (v); and
  (vii) drying the evaporated solid phase residue, thus obtaining a dry powder.

A corresponding preparation, wherein one or more of the different aerial parts of the plants are used.

A corresponding preparation, wherein the soil plant parts are used.

A corresponding preparation that comprises one, more or all of the following compounds:
  2,4,5,7-Tetrathiaoctane;
  2,4,5,6,8-Pentathianonane;
  2,3,5,7,8-Pentathiadecane;
  2,4,6-Trithiaheptane; and
  2,4-Dithiapentane.

A corresponding preparation further comprising solid, pulverulent carrier materials or fillers, and/or additives that augment or regulate the effect of the preparation.

A preparation in form of an aqueous solution or suspension based on a dry preparation as specified above.

A corresponding preparation, wherein the concentration of crude extract or the dry powder is in the range from 0.2 g/l to 2 g/l, preferably from 0.5-1.0 g/l.

A composition comprising a first plant preparation as specified above and at least a second plant preparation in form of a crude extract, dry powder or an aqueous suspension or solution thereof, said second plant preparation exerting an additional plant protective effect on the plants or parts thereof treated with the composition.

A corresponding composition, wherein said second plant preparation derives from a species from the genus *Agapanthus*, preferably from *A. africanuns* and is obtained by analogous process steps as said first plant preparation.

A corresponding composition, wherein the second plant preparation derives from a mixture of species of the Pink family and Alfalfa species, wherein the proportion by weight of the dried Pink species material is between 80 and 99%, said second plant preparation being obtained by analogous process steps as said first plant preparation.

A three-component composition comprising
  (i) a first plant preparation as specified above,
  (ii) a second plant preparation deriving from a species from the genus *Agapanthus*, and
  (iii) a third plant preparation deriving from a mixture of species of the Pink family and Alfalfa species, wherein the proportion by weight of the dried Pink species material is between 80 and 99%, each preparation in form of a crude extract, dry powder or an aqueous suspension or solution thereof, said second and third plant preparation exerting an additional plant protective effect on the plants or parts thereof treated with the composition.

The use of the preparation/composition as specified above as a biological plant protective agent.

The use of said preparation/composition, wherein the biological plant protective agent is an antimicrobial agent, such as an antibacterial agent or an antifungal agent, preferably an antifungal agent.

The use of said preparation, wherein the antifungal agent inhibits mycelial growth of fungi.

The corresponding use for preventing infection of crop by fungi under field conditions.

The use of said preparation/composition, wherein the biological plant protective agent is a bio-stimulatory agent, which preferably elicits growth induction and/or induces systemic acquired resistance in plants or plant parts treated with the agent.

The corresponding use, wherein the bio-stimulatory agent elicits stimulation of seedling growth.

A compound isolated from a said preparation as specified above selected from the group consisting of:
  $^1CH_3S^3CH_2SSS^7CH_2S^9CH_3$ (2,4,5,6,8-Pentathianonane)
  $^1CH_3SS^4CH_2S^6$ $CH_2S^8CH_2S^{10}CH_3$ (2,3,5,7,8-Pentathiadecane)
  $^1CH_3S^3CH_2S^5CH_2S^7CH_3$ (2,4,6-Trithiaheptane)
  $^1CH_3S^3CH_2S^5CH_3$ (2,4-Dithiapentane).

A composition suitable for plant protection comprising at least two, preferably all of the compounds selected from the group consisting of:
2,3,5,7,8-Pentathiadecane; 2,4,5,6,8-Pentathianonane; 2,4,6-Trithiaheptane; 2,4-Dithiapentane; 2,4,5,7-Tetrathiaoctane.

The use of said compounds/compositions as biological plant protective agent.

The use of said compounds/compositions as antifungal agent, which preferably inhibits the mycelial growth of fungi.

A process for the preparation of a crude extract or a dry powder preparation or aqueous suspensions or solutions thereof as defined in any of the claims 1-10, characterized in that the following steps are carried out:

(i) drying the plant material at 30-40° C. to the exclusion of sun light;
(ii) grinding the dried plant material to a grit size between 0.2-2 mm, preferably 1 mm
(iii) soaking the ground material in a polar organic solvent, such as methanol or ethanol, thus forming a suspension/solution;
(iv) performing a stirred extraction of the suspension and separating the supernatant from the solid phase;
(v) repeating step (iii) and (iv) at least one additional time;
(vi) combining the soluble organic phases of step (iv) and removing the organic solvent by vacuum evaporation at 30-40° C., thus obtaining the crude extract residue;

and in the case of the preparation of an aqueous preparation;
(vii) suspending the resultant crude extract in water in a suitable concentration;

or alternatively by the steps:
(ia) drying the plant material at 30-40° C. to the exclusion of sun light;
(iia) grinding the dried plant material to a grit size less than 0.1 mm,
(iiia) soaking the ground material in a first polar organic solvent, such as ethanol or methanol, thus forming a suspension/solution;
(iva) performing a stirred extraction of the suspension;
(va) evaporating the solvent without prior separation of the solid phase from the soluble organic phase;
(via) soaking the evaporated solid phase residue in a second polar organic solvent and repeating steps (iva) and (va);
(viia) drying the evaporated solid phase residue, thus obtaining a dry powder;

and in the case of the preparation of an aqueous preparation,
(viii) suspending the resultant dry powder in water in a suitable concentration.

A corresponding, wherein the polar organic solvent of step (iii) is 90-100% methanol or ethanol.

A corresponding process, wherein said the first polar organic solvent of step (iiia) is 90-100% methanol and said second polar organic solvent of step (via) is 90-100% ethanol.

A corresponding process, wherein the respective solvent is used for extractions in a concentration of 1.0-3.0 ml/g dry weight of the ground plant material.

A corresponding process, wherein the concentration of the crude extract or the dry powder material in the aqueous solution or suspension is between 0.2 g/l and 2 g/l, preferably between 0.5 g/l and 1 g/l.

DETAILED DESCRIPTION OF THE INVENTION (A) General Definitions

Above and below terms and expressions are used which have according to the understanding of the this invention the following meanings:

The term "plant protecting agent" or "plant protective agent" means, if not otherwise specified, any kind of synthetic or natural agent, product, extract, composition that is effective in a broad sense for the protection and health of a plant against infection and damages by pathogens in vitro and/or in vivo. The term includes agents, products, extracts, compositions or single isolated components of extracts which may show a couple of different biological activities and/or properties, such as antimicrobial, antiviral, antifungal, and bio-stimulatory activity/efficacy, growth inducing/promoting activity (with respect to the plant to be protected), growth inhibitory activity (with respect to the plant(s) competitive to the plant to be protected), systemic and/or immunological acquired resistance inducing/promoting activity, and allelopathy inducing/promoting activity.

The term "biological plant protection" means according to the invention, if not otherwise specified, that the protection of a plant is achieved by naturally occurring or naturally derived substances or sources preferably from plants, and not by synthetic or chemical means or agents, which do not occur in nature, preferably plants or part of plants.

The term "biological plant protecting (protective) agent" is thus, consequently a plant extract, a plant preparation, a composition based on plants or parts thereof, or an agent isolated from a plant extract/preparation/composition, which all show significant efficacy against a plant pathogen in vitro and/or in vivo. This term includes also chemically synthesized compounds which are structurally and functionally identical with the isolated naturally derived compound, but excludes expressively chemically synthesized pesticides and related compounds having no natural derived counterpart.

The term "pesticide" means according to the invention, if not otherwise specified, not naturally derived or occurring, synthetic compounds, agents or compositions which have plant protecting efficacy.

The term "plant pathogen" means a compound or composition or living material, such as a microorganism (including viruses), which causes disease or damage to the plant. In a narrower scope of the invention the term is focused to pathogenic microorganisms including metabolic products of these microorganisms.

The term "antimicrobial" according to the invention encompasses an efficacy or activity against microorganisms, including viruses, bacteria and fungi, that reduces or eliminates in vitro and/or in vivo the (relative) number of active microorganisms which attack the plant or parts thereof to be protected. Thus, the term includes the terms "antiviral", "antibacterial", and "antifungal". An "antimicrobial agent" according to the invention is a biological plant protecting agent as specified above, which prevents or reduces infections or damages of a plant caused by a pathogenic microorganism.

The term "antibacterial" means according to the invention an activity or efficacy (e.g. of an agent or extract, etc.), that reduces or eliminates the (relative) number of active bacteria. An "antibacterial agent" according to the invention is a biological plant protecting agent as specified above, which prevents or reduces in vitro and/or in vivo infections or damages of a plant caused by a pathogenic bacterium.

The term "antiviral" means according to the invention an activity or efficacy (e.g. of an agent or extract, etc.), that reduces or eliminates the (relative) number of active viruses. An "antiviral agent" according to the invention is a biological plant protecting agent as specified above, which prevents or reduces in vitro and/or in vivo infections or damages of a plant caused by a pathogenic virus.

The term "antifungal" means according to the invention an activity or efficacy (e.g. of an agent or extract, etc.), that reduces or eliminates the (relative) number of active fungi. An "antifungal agent" according to the invention is a biological plant protecting agent as specified above, which prevents or reduces in vitro and/or in vivo infections or damages of a plant caused by a pathogenic fungus. The antifungal activity may lead to the inhibition of mycelial growth as well as spore germination of fungi.

The term "bio-stimulatory" means according to the invention, if not otherwise specified, an activity or efficacy which stimulates, increases or improves many different processes in the plant or plant parts, such as improved generation of growth promoting substances like sugars and amino acids, improved adequate supply of cells with available nutrients and growth regulators, enhanced cell metabolism, improved cell decontamination, enhanced immune defense, promotion of growth and yield, induction of systemic acquired resistance (SAR), inhibition of growth and yield of competing plants (allelopathy). The bio-stimulatory activity can be caused by agents, plant extracts and compositions including metabolic compounds synthesized by the plant to be protected after induction of their synthesis by said bio-stimulatory agent. A "bio-stimulatory agent" according to the invention is a biological plant protecting agent as specified above, which shows the above-specified bio-stimulatory properties in a plant treated with this agent in vitro and/or in vivo.

A "plant growth regulator" is a compound or a mixture of substances either natural or synthetic, that modifies or controls one or more specific physiological processes within a plant. If the compound is produced within the plant it is called a plant hormone e.g. auxins, gibberellins, abscisic acid and ethylene.

"SAR" (Systemic Acquired Resistance) occurs in a plant or parts thereof according to the invention if it shows induction or enhancement of activity of defense or protection related enzymes (PR-proteins). Such enzymes include, for example, peroxidase, $\beta$-1,3-glucanse and NADPH oxidase.

(B) Plant Description

*Tulbaghia violacea* is known as wild garlic and the name stems from the fact that, although its taste is close to that of real garlic, it is supposed not to leave behind embarrassing bad-breath odours. The species name "*violacea*" comes from the Latin for "violet". It belongs to the family Alliaceae (Lilliaceae). *Tulbaghia violacea* originated in South Africa. It is grown as an ornamental in botanical gardens and in home gardens all over southern Africa and it is cultivated in some overseas countries such as the USA and the UK. *Tulbaghia violacea* has been used in foods as a garlic replacement. Wild garlic is traditionally used for fever and colds, but also for asthma and tuberculosis. The leaves are used to treat cancer of the oesophagus. *Tulbaghia violacea* is a spreading, vigorous, clump-forming perennial herb with grass-like foliage and corm-like rhizomes. Inflorescence consists of 3-40 flowered umbels. The flower heads are borne on long, slender, solitary stalks that stand well above the foliage. The stalked flowers are tiny and grouped in umbels at the tips of the stems. The plant's mature height is 30 to 60 cm. The flowers are of a lilac purple or violet colour. *Tulbaghia violacea* is very easy to grow and will endure neglect for many years. The plants form clumps that do not need to be divided unless the flowers show signs of deterioration. The plant is able to thrive in quite poor soil or in ordinary garden soil, but grows more successfully in good loam soil mixed generously with compost. Drainage should be good, particularly in areas of winter rainfall. The plants require moisture at regular intervals throughout the year, but more particularly during summer. They are hardy and may be grown in cold places. Propagation is by seeds or divisions.

(C) Microorganisms

Seven common South African plant fungal pathogens are chosen to test for the fungitoxic properties of the plant extracts. These fungal pathogens included *Botrytis cinerea* Pers.:Fr. (Hyphomycetes), *Fusarium oxysporum* Schlechtend.:Fr. (Hyphomycetes), *Sclerotinia rollfsii* Sacc. (Agonomycetes), *Rhizoctonia solani* Kühn (Agonomycetes), *Botryosphaeria dothidea* (Moug.: Fr.) Ces. & De Not. (Loculoascomycetes), *Pythium ultimum* Trow (Oömycetes) and *Mycosphaerella pinodes* (Berk.+Blox.).

Plant pathogenic bacteria used in this study include *Agrobacterium tumefaciens* (Smith and Townsend), *Clavibacter michiganensis* (Smith), *Erwinia carotovora* pv. *carotovora* (Jones), *Xanthomonas campestris* Pammel pv. *Phaseoli* (Dawson), *Ralstonia solanacearum* (Smith) and the human bacterium *Moraxella catarrhalis* (Frosch+Kolle).

(D) Screening of Crude Extracts from *Tulbaghia violacea* for In Vitro Antimicrobial and Biostimulatory Activity 1. General Extracts from certain plants of *T. violacea* possess antimicrobial and bio-stimulatory properties and have the potential to be exploited as natural products in the control of plant diseases or to promote crop growth.

The bio-stimulatory potential of the extracts was evaluated in vitro by following their effect on the respiration rate of a monoculture yeast cells, the germination of Cress seeds as well as radicle and coleoptile growth of Cress seedlings.

2. Recovery of Crude Extract from Dried Plant Material

After drying and grinding, 7.96% (w/w) aerial part dry material and 26.1% (w/w) below soil part dry material can be obtained from the original fresh *T. violacea* material collected (Table 1). After extraction, 14% (w/w) dry crude material can be recovered from the dried aerial part material while 6.7% (w/w) dry crude material can be recovered from the dried below soil part material.

TABLE 1

Recovery of crude extract from dried plant material

| Plant Organs | Fresh Mass (g) | Mass (g) after drying | Mass (g) after grinding | Mass (g) of methanol extract | % Recovery of crude extract from dry material |
|---|---|---|---|---|---|
| Aerial parts | 16032.1 | 1284.8 | 1275.9 | 179.14 | 14 |
| Below soil parts | 16864.8 | 4529.0 | 4392.8 | 293.46 | 6.7 |

3. In Vitro Antibacterial Activity of *T. violacea* Crude Extracts

Out of the six phytopathogenic bacteria used as test organisms, the growth of three plant pathogens (*C. michiganensis, R. solanacearum, X. campestris*) were significantly inhibited by both below soil and aerial part crude extracts, the results for *M. catharrhalis* are not shown (Table 2).

TABLE 2

In vitro growth inhibition of plant pathogenic bacteria by crude extracts of different *Tulbaghia violacea* organs. Mean Inhibition Zone Diameter (mm)

| Extracts | Bacteria | | | | | |
|---|---|---|---|---|---|---|
| | *Clavibacter michiganensis* | *Pseudomonas syringae* | *Erwinia caratovora* | *Agrobacterium tumefaciens* | *Ralstonia solanacearum* | *Xanthomonas campestris* |
| Aerial part | 8.7 ± 1.7a | 0 ± 0a | 0 ± 0a | 0 ± 0a | 9.8 ± 1.2ab | 12.2 ± 2.4ab |
| Below Soil part | 7.3 ± 1.1a | 0 ± 0a | 1 ± 1.41a | 0 ± 0a | 15.4 ± 0.7a | 18.2 ± 0.23a |
| DMSO Control | 0 ± 0b | 0 ± 0a | 0 ± 0a | 0 ± 0a | 0 ± 0c | 0 ± 0c |

The crude aerial and below soil part extracts of *T. violacea* reveal significant bio-stimulatory activity on the respiration rate of yeast cells as well as radicle and coleoptile growth of Cress seedlings, but have no effect on the germination of the seeds.

The crude extracts also show some in vitro antibacterial activity against four of the seven bacteria tested.

The crude extracts elicit a significant (P<0.05) antifungal activity against six economically important phytopathogenic fungi. The crude extracts outperformed the standard fungicide used as a positive control and completely inhibit the mycelial growth of five of the six fungi, including the highly resistant *Pythium ultimum*.

The other three bacteria were much more resistant to treatment with the crude extracts and were not affected by the extracts at all.

4. Antifungal Activity of *T. violacea* Crude Extracts

The below soil part extract of *T. violacea* completely inhibited (100%) the mycelial growth of *B. cinerea, S. rolfsii* and *P. ultimum* and showed a very high inhibition (>95%) for both *F. oxysporum* and *R. solani*. The lowest inhibition (90%) observed was against *B. dothidea* (FIG. 1). Mycelial growth inhibition by the aerial part extract was also very high (>95%) for *B. cinerea, S. rolfsii* and *P. ultimum* and >80% for *R. solani* and *B. dothidea*. *Fusarium oxysporum* (75% inhibition) was most resistant against treatment with the aerial part extract.

Statistically, both the aerial and below soil part crude extracts of *T. violacea* outperformed the standard fungicide significantly (P<0.05) in terms of mycelial growth inhibition of four out of the six test fungi. However, both extracts compared favourably with the standard fungicide in terms of mycelial growth inhibition.

Figure 2:
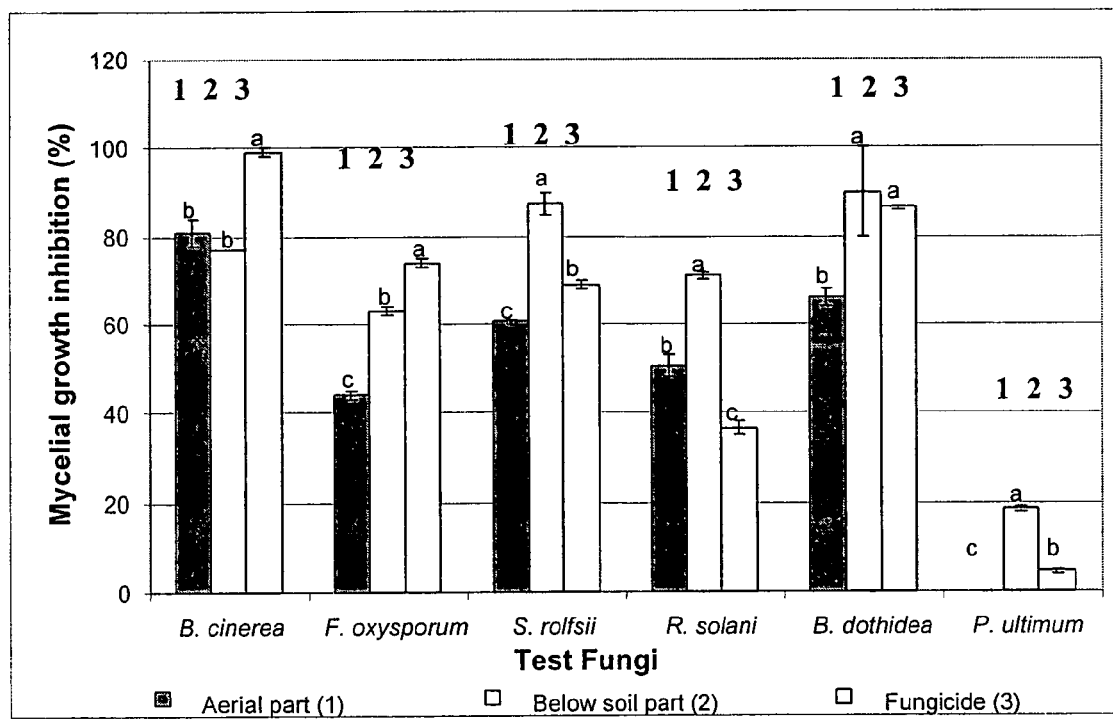

FIG. 2 illustrates the antifungal activity in vitro of the same two crude extracts of *T. violacea* after storage at −20° C. for one year. Compared to the standard fungicide, a decrease in the antifungal activity of >30% was observed for both the aerial and below soil part crude extracts stored in a freezer at −20° C. for one year.

Table 3 shows the average antifungal activity in vitro of different plant organs of *T. violacea* extracts (1 mg/ml) in vitro as compared the standard fungizide Eria®.

TABLE 3

In vitro antifungal activity of crude extracts from different organs of *T. violacea*.

| Plant Y | Root | 100a ± 0 | 100a ± 0 | 100a ± 0 | 100a ± 0 | 99a ± 1 | 100a ± 0 |
|---|---|---|---|---|---|---|---|
| | Above ground parts | 99a ± 1 | 76c ± 3 | 100a ± 0 | 85bc ± 3 | 86bc ± 2 | 100a ± 3 |
| | *Standard | 100a ± 0 | 70c ± 3 | 68c ± 4 | 38 ± 2 | 87bc ± 3 | 4f ± 1 |

Standard broad spectrum fungicide; Carbendazim/difenoconazole (Eria®)
Different letters following values indicate statistical significant differences.

5. Biostimulatory Activity of *T. violacea* Crude Extracts

Figure 3:
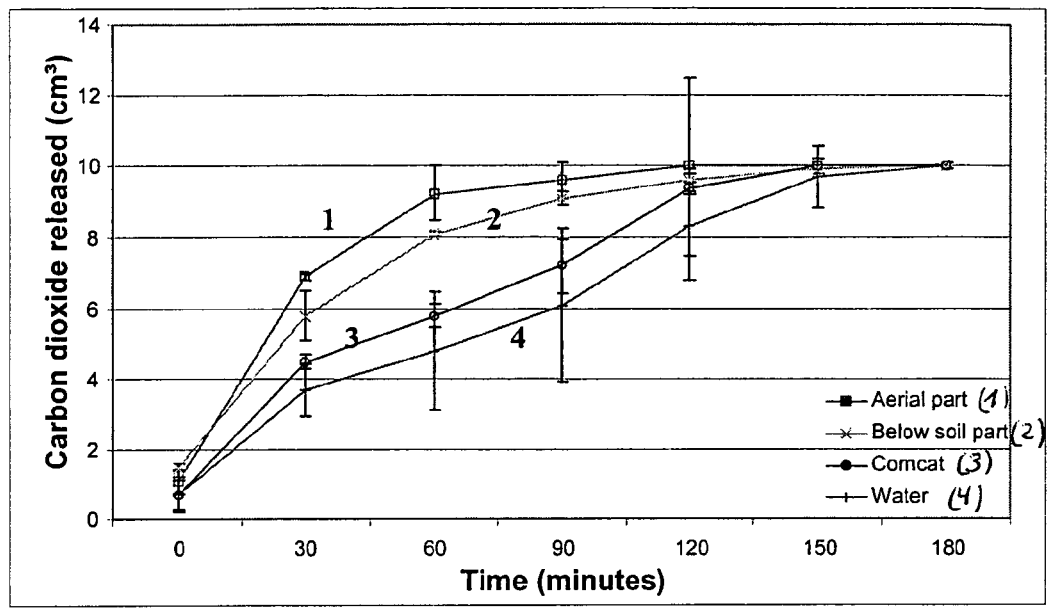

Both the aerial and below soil part crude extracts of *T. violacea* increased the respiration rate of a monoculture yeast cells markedly over the first 90 minutes of incubation (FIG. 3) compared to both the water and the ComCat® controls. However, after 120 minutes of incubation the differences in respiration rate were less pronounced as the maximum rate was probably reached. Although the commercial bio-stimulant, ComCat® also had an increasing effect on the respiration rate of yeast cells, this was not as marked as the effect of both crude extracts of *T. violacea*.

Statistically no significant differences (P<0.05) in the percentage germination of Cress seeds between treated and non-treated seeds were observed (Table 4).

TABLE 4

Mean percent (%) germination of Cress seeds, treated with aerial and below soil part extracts of *T. violacea*, at 25° C. over a 96 hour incubation period. ComCat ® and distilled water served as controls.
Mean % Germination

| Aerial parts | Below soil parts | ComCat ® | Water |
|---|---|---|---|
| 68.33 ± 8.5a | 71.67 ± 10.27a | 71.67 ± 6.24a | 63.33 ± 10.27a |

Figure 4:
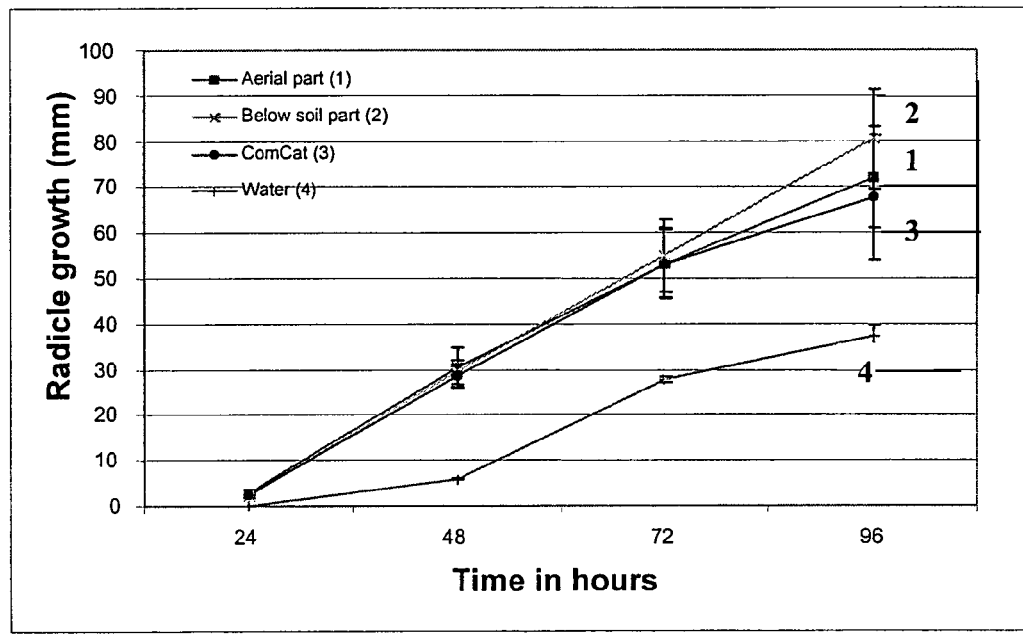
Figure 5:
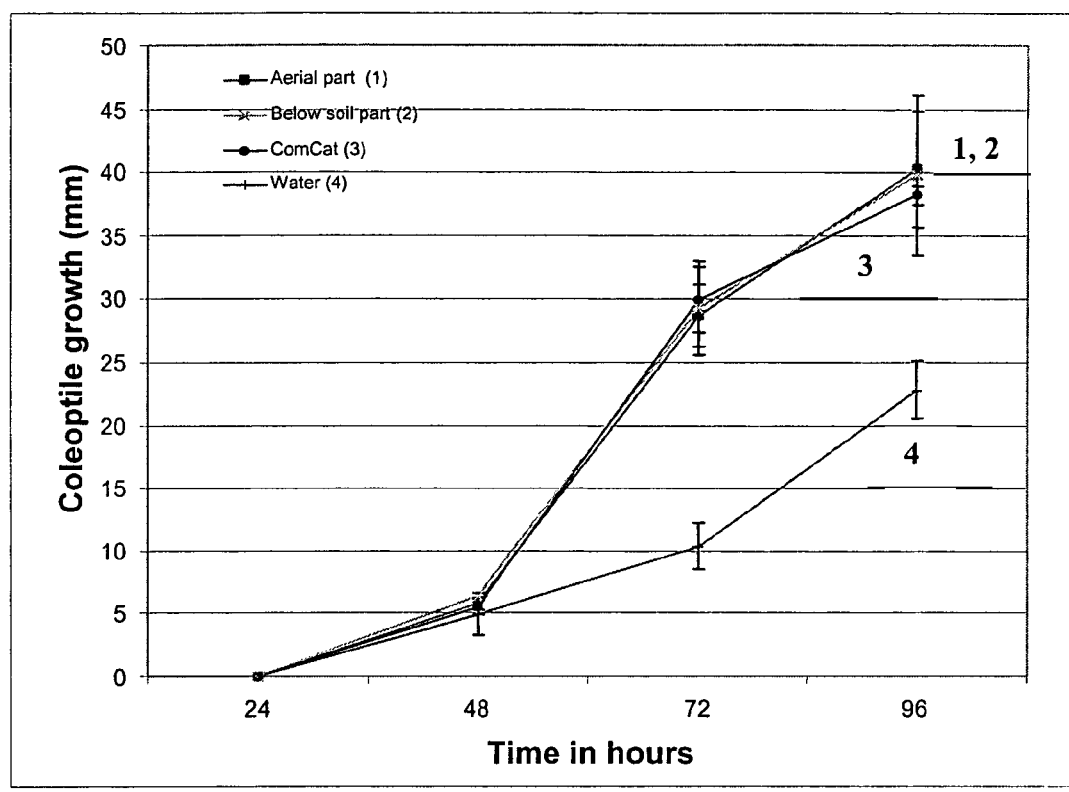

However, both the aerial and below soil part crude extracts of *T. violacea* had a significant stimulatory effect on both coleoptile and root growth of Cress seedlings when compared to the water control. There was no significant difference in bio-stimulatory activity between the extracts and the commercial biostimulant ComCat.® (FIGS. 4 and 5).

(6) Antifungal Properties of *A. africanus* Crude Extracts Combined with Extracts from *Tulbaghia violacea*

A crude extract or a dry powder of a species of the genus *Agapanthus*, such as *A. africanus*, is prepared analogously to the methods described here for *T. violacea*. The extracts or dried powders are mixed in a 1:1 ratio and aquous solutions are applied in different concentrations varying from 0.25 mg/ml to 2 mg/ml.

It is interesting to note that a 50:50 mixture of the two extracts, applied at 0.5 mg/ml, shows total control of the six test fungi (Table 5), whereas in comparison hitherto, applying separately the two-fold concentration (1 mg/ml) of the *A. africanus* preparation or the *T. violacea* preparation, inhibition of the mycelial growth of the test fungi is not complete. Even a concentration of 0.25 mg/ml of a combined extract/dry powder preparation (1:1) leads to an over-all inhibition of the same fungus system of more than 90%, indicating that significant synergism is effective in the combination system. The same effect is observable with other plant-protecting agents.

TABLE 5

In vitro antifungal activity of crude extracts from the above ground parts of *T. violacea* (X) and *A. africanus* (Y) and used together in a 1:1 ratio and applied at 0.5 mg/ml.

| Extract | | % Mycelial Growth Inhibition for different fungi Fungus | | | | | |
|---|---|---|---|---|---|---|---|
| Mix (50:50) | Plant material | *Botrytis cinerea* | *Fusarium oxysporum* | *Sclerotium rolfsii* | *Rhizoctonia solani* | *Botryosphaeria dothidea* | *Pythium ultimum* |
| Plant X + Plant Y | Above ground | 100a ± 0 | 100a ± 0 | 100a ± 0 | 100a ± 0 | 100a ± 0 | 100a ± 2 |

TABLE 5-continued

In vitro antifungal activity of crude extracts from the above ground parts of *T. violacea* (X) and *A. africanus* (Y) and used together in a 1:1 ratio and applied at 0.5 mg/ml.

| Extract | | % Mycelial Growth Inhibition for different fungi Fungus | | | | | |
|---|---|---|---|---|---|---|---|
| Mix (50:50) | Plant material | *Botrytis cinerea* | *Fusarium oxysporum* | *Sclerotium rolfsii* | *Rhizoctonia solani* | *Botryosphaeria dothidea* | *Pythium ultimum* |
| (50:50) | parts Standard | 100a ± 0 | 70c ± 3 | 68c ± 4 | 38 ± 2 | 87bc ± 3 | 4f ± 1 |

Standard broad spectrum fungicide; Carbendazim/difenoconazole (Eria®)
Different letters following values indicate statistical significant differences.

(7) Summary Results

The in vitro fungitoxic effects of both the aerial and below soil part crude extracts of *T. violacea* are significantly higher than that of the synthetic fungicide. All test fungi are sensitive to the extracts emphasizing their broad spectrum potential. In light of the fact that *T. violacea* is easy to grow and can endure neglect for many years; it is a strong candidate for large scale cultivation as a donor plant in the event that the production of a natural fungicide is considered.

The decline in the fungitoxicity of one-year old *T. violacea* extracts stored at −20° C. is environmentally desirable for use under field conditions. In light of the current emphasis on organic farming, the development of a natural fungicide from *T. violacea* extracts should strongly be considered. The fact, that the aerial part extract is just as potent as the below soil part extract in inhibiting the mycelial growth of a broad spectrum of plant pathogens, indicates that cultivated plants could be harvested in a non-destructable manner. Below soil parts can then remain in the soil for producing the next season's harvest in a sustainable manner.

Further, both the aerial and below soil part crude extracts of *T. violacea* and the commercial bio-stimulant ComCat® significantly increase the respiration rate of a monoculture yeast cells over the first 90 minutes and slow down after 120 minutes of incubation, indication a significant bio-stimulatory effect. This means that both extracts and ComCat® stimulate the production of carbon dioxide more than water, i.e. increase the respiration rate making more energy available for germination and seedling growth. Consequently, a positive correlation seem to exist between high respiration rate and seedling growth as both organ crude extracts significantly stimulate radicle and coleoptile growth of Cress seedlings over a period of 96 hours compared to the water control. In this study no significant difference between the crude extracts and ComCat® in stimulating seedling growth can be observed, bringing the *T. violacea* extracts on par with the commercial bio-stimulant. Statistically ($P<0.05$), Cress seed germination show no significant response to both plant organ extracts compared to both the ComCat® and water controls. This study reveals that the extracts of *T. violacea* indeed possess bio-stimulatory properties, especially with respect to the enhancement of seedling growth. The latter provides a challenge for full scale research on this issue in order to additionally evaluate the application potential under field conditions. In summary, the above average broad spectrum antifungal activity of crude *T. violacea* extracts as well as the lesser antibacterial activity and the significant bio-stimulatory properties lead to the conclusion that the crude extract from *T. violacea* are favourable for the use of these plants for biological plant protection.

Combined extracts/dry powders based on preparations from two or more plants having plant protecting properties, wherein at least one is *T. violacea*, show over a broad range antifungal and bio-stimulatory efficacy at least in vitro based on synergistic effects.

(E) In Vivo Control of *Mycosphaerella pinodes* on Pea (*Pisum sativum*) Leaves by Extracts from *Tulbaghia violacea*

1. General

*Ascochyta* blight of pea (*Pisum sativum*) caused by *Mycosphaerella pinodes* (Berk & Blox.) Vesterger, occurs worldwide and causes yield losses of up to 30%. It is a disease of economic importance and can cause serious yield reduction of peas grown for both human and animal consumption. It is a major constraint to field pea production and is the most destructive foliar pathogen of pea in many countries. The fungus infects pea seedlings as they emerge, causing girdling stem lesions. Infection of stems results in small brown streaks that later turn blue-black in colour which reduce field pea populations and increase lodging. Necrotic lesions develop on all aerial parts of the pea plant, including the pods, grown from contaminated seeds. *Mycosphaerella pinodes* is spread via pycnidiospores throughout the season. After germination of spores, the fungus grows over the plant surface before forming an aspersorium and penetrating the cuticle. Symptoms may appear as early as 24 hours after infection under optimal conditions and are characterized by brown to purplish, coalescing lesions on aerial tissue. Non-germinated spores remain viable for up to 21 days under dry conditions. Infection and disease development are highly dependent on temperature and leaf wetness.

A crude methanol aerial part extract of *T. violacea* is tested against *Mycosphaerella pinodes*, the cause of black spot or *Ascochyta* blight in peas (*Pisum sativum*). The crude extract prevents *M. pinodes* spore infection of the pea leaves when the leaves are inoculated with spores both before and after treatment with the extract, confirming complete inhibition of spore germination. The crude extract shows no phytotoxic reaction on the leaves, even at the highest concentration applied.

2. In Vivo Antifungal Activity of Preparations of *T. violacea* Under Glasshouse Conditions Treatment of detached pea leaves with the crude extract first, followed by spore inoculation 30 minutes later, totally suppress lesion formation on the leaves (Table 6) at all concentrations tested. This is also the case for the Standard fungicide treatment before inoculation. However, when the leaves are inoculated with the spores first, followed by treatment with different concentrations of the crude extract, lesions form on the leaves treated with the low extract concentrations of 0.25 mg/ml and 0.5 mg/ml (2.38 and 1.88 mm respectively; Table 6). Spore inoculation followed by crude aerial part extract treatment at the same two low concentrations showed a significantly ($P<0.05$) better suppression of lesion development than spore inoculation followed by treatment with the standard fungicide (3.63 mm), but the latter significantly inhibited lesion formation when compared to the control (spore inoculation only, 9.44 mm). At concentrations of 1.0 and 2.0 mg/ml the aerial part extract of *T. violacea* totally inhibited infection of pea leaves by *M. pinodes* spores (Table 6).

The in vivo screening trial using pea leaves inoculated with *M. pinodes* spores either before or after treatment with the plant extracts, the crude extract of *T. violacea* may inhibit spore germination of *M. pinodes* 100% at the lowest concentration used (0.25 mg/ml), when the extract was applied before spore inoculation. This is a very favourable value comparing with other plants, such as extracts from *Agapanthus africanus*, which show 100% inhibition at a concentration not before 1 mg/ml.

TABLE 6

In vivo activity of crude extracts from the above ground parts of *T. violacea* against *Mycospaerella pinodes* on pea leaves.

| Plant Y | Extract sprayed on leaves first and spore inoculation followed 30 min later | 2 mg ml$^{-1}$ | 0 | 100% |
|---|---|---|---|---|
| | | 1 mg ml$^{-1}$ | 0 | 100% |
| | | 0.5 mg ml$^{-1}$ | 0 | 100% |
| | | 0.25 mg ml$^{-1}$ | 0 | 100% |
| | | *Fungicide standard | 0 | 100% |
| | | Spores only | 9.44 | — |
| | Leaves inoculated with spores first and extracts sprayed on leaves 30 min later | 2 mg ml$^{-1}$ | 0 | 100% |
| | | 1 mg ml$^{-1}$ | 0 | 100% |
| | | 0.5 mg ml$^{-1}$ | 1.88 | 80% |
| | | 0.25 mg ml$^{-1}$ | 2.38 | 75% |
| | | *Fungicide standard | 3.63 | 62% |
| | | | 9.44 | — |

*Standard broad spectrum fungicide; Carbendazim/difenoconazole (Eria®)

(3) Phytotoxic Effects of Preparations from *T. violacea* on Pea Leaves Under Glasshouse Conditions The in vivo phytotoxicity rating of the crude extract of the aerial parts of *T. violacea*, in terms of its interaction with and potential to induce necrosis in pea leaves, revealed that the crude extract was not phytotoxic even at the highest concentration tested (Table 7) and the symptomless effect of the extract was similar to that of the water and standard fungicide controls.

TABLE 7

Mean foliar phytotoxicity symptom rating on a six-category scale following direct inoculation of fourth node pea leaflets with different concentrations of a crude aerial part extract of *Tulbaghia violacea*.

| Plant extract applied as Foliar treatment | Extract concentration | Mean lesion size (mm) on pea leaf |
|---|---|---|
| Aerial part extract alone | 2 mg ml$^{-1}$ | 0 ± 0a |
| | 1 mg ml$^{-1}$ | 0 ± 0a |
| | 0.5 mg ml$^{-1}$ | 0 ± 0a |
| | 0.25 mg ml$^{-1}$ | 0 ± 0a |
| Standard fungicide alone | | 0 ± 0a |
| Water control | | 0 ± 0a |
| Spore suspension only | | 4 ± 0.29b |

Values designated with different letters differed significantly (P<0.05) according to the Least Significant Difference (LSD) statistical procedure.

(4) General Discussion

None of the four concentrations (0.25, 0.5, 1.0 and 2.0 mg/ml) of a crude *T. violacea* aerial part extract is phytotoxic to pea (*Pisum sativum*) leaves. When the pea leaves are treated with the extract first and followed by spore inoculation 30 minutes later, the extract suppresses the germination of *M. pinodes* spores totally even at the lowest concentration of 0.25 mg/ml. This indicates that the crude aerial part extract of *T. violacea* shows potential to be used as a preventative measure against *Ascochyta* blight caused by *M. pinodes* on pea leaves without causing injury to the plant. According to Benner (1993, *Pesticide Science* 39:95-102), phytotoxicity is a decisive factor in evaluating plant extracts for their application potential as natural pesticides in agriculture.

Moreover, when the pea leaves were inoculated with *M. pinodes* spores 30 min. before treatment with the crude *T. violacea* aerial part extract, the 1 mg/ml concentration totally inhibited spore germination and subsequent lesion formation indicating that the crude extract also possesses the potential to be used as a corrective measure against *Ascochyta* blight.

The results obtained in this study confirm the potential of a crude *T. violacea* to control fungal infections of crops, at least under controlled conditions. Even the four times higher concentration that was needed to correctively inhibit *M. pinodes* spore germination, compared to the lower concentration that was needed as a preventative measure, still falls within an economically viable range of 1 g/l. Considering that an average of 400 litre fungicide solution is normally applied per hectare under agricultural field conditions, this concentration is in line with current commercially available fungicides. A minimum inhibitory concentration (MIC) of 1 g/l is also much lower than the MIC reported for a crude bulb extract of *Eucomis autumnalis* (Pretorius et al., 2002, *Annals of Applied Biology* 141:125-131).

These findings are valuable for assessing the potential application of the crude *T. violacea* aerial part extract in an integrated pest management (IPM) system in terms of minimizing crop losses caused by *Ascochyta* blight.

(5) Control of *Sorghum* Covered and Loose Smuts by an Aerial Part Crude Extract of Under *Tulbaghia violacea* Field Conditions

*Sorghum* (*Sorghum bicolor* L. Moench) is an important source of food in many non-developed countries and serves as staple food for the majority of people. It is predominantly grown in small-scale production systems under a wide range of environmental conditions. However, production of sorghum is less than 1.0 ton/ha due to various reasons. *Sorghum* covered kernel (*Sporisorium sorghi* Link, G. P. Clinton) and loose kernel smuts (*Sporisorium cruenta* Kuhn, A. A. Potter) are major factors that account for low yields. Both diseases occur frequently where sorghum is grown without treating seeds against these two pathogens.

An aerial part crude extract of *Tulbaghia violacea* can be evaluated against sorghum covered (*Sporisorium sorghi*) and loose (*Sporisorium cruentum*) kernel smuts under field conditions. The crude extract is applied at the rate of 2.0 mg/ml in lots of 90.0 g sorghum seeds by artificially inoculating separate sets of sorghum seed with smut spores at a rate of 0.5% (w/w). A standard fungicide, Thiram (65 W), is applied as a seed treatment at the rate of 0.25%/kg of sorghum seed and served as a positive control. Disease incidence observed during harvest is expressed as a percentage of infected plants. Both treatments significantly (P<0.05) reduce the incidence of both loose and covered kernel smuts and resulted in significant yield increases compared to the untreated control. Covered and loose smut incidence and yield can be significantly correlated ($R^2$=0.92, P<0.05) and ($R^2$=0.75, P=75). From these results it is envisaged that the aerial part crude extract of *T. violacea* has the potential to be developed into an environmentally friendly bio-fungicide for application in small scale farming systems where synthetic chemicals are out of reach of the average subsistence farmer.

Treatment of sorghum seeds with an aerial part crude extract of *T. violacea* before planting completely (100%) (P<0.05) reduced the incidence of covered smut (Table 8a) and significantly reduced loose smut incidence (Table 8b) compared to the corresponding untreated controls, and compared favourably with the synthetic fungicide, Thiram in the control of covered kernel smut.

TABLE 8a

Effect of an aerial part crude extract of *T. violacea* on the percentage covered kernel smut disease incidence in *sorghum* under field conditions.

| Treatments | Mean plant Population | % Mean smut I Incidence | Yield (ton ha$^{-1}$) |
|---|---|---|---|
| Aerial part extract | 191 ± 6a | 0 ± 0a | 5.0 ± 1a |
| Thiram | 188 ± 12a | 0 ± 0a | 4.8 ± 0.6a |
| Control | 174 ± 12a | 9 ± 0b | 2.9 ± 2.1b |

TABLE 8b

Effect of an aerial part crude extract of *T. violacea* on the percentage loose kernel smut disease incidence in *sorghum* under field conditions.

| Treatments | Mean plant Population | % Mean smut I Incidence | Yield (ton ha$^{-1}$) |
|---|---|---|---|
| Aerial part extract | 175 ± 0a | 14 ± 3a | 4 ± 1.7a |
| Thiram | 175 ± 0a | 0 ± 0b | 3.9 ± 1.3a |
| Control | 175 ± 0a | 32 ± 8c | 2.5 ± 1b |

Values designated with different letters differed significantly (P<0.05) according to Duncan's Least Significant Difference (LSD) statistical procedure.

Inoculation of pre-planted sorghum seed with covered or loose smuts spores, without also treating the seeds with either Thiram or the crude *A. violacea* extract (untreated controls), significantly decreased the final yields (Tables 7a and 7b). In the case of covered smut the yield loss was 46.7% and, in the case of loose smut, 55.2%. However, in both cases, there was no significant difference in yield between plots treated with either Thiram or the *T. violacea* crude extract. A significant difference in yield between the Thiram treated and untreated controls was also observed in both cases.

The percent covered and loose smuts incidences were negatively correlated ($R^2$=−0.92 and −75 respectively) with sorghum grain yield indicating the negative impact both smut diseases had on the yield.

Pre-treatment of sorghum seeds with an aerial part crude extract of *T. violacea* at a rate of 2 g/1 completely prevents infection by covered kernel and significantly reduces the incidence of loose kernel smuts under field conditions. This is comparable favourably with the decrease in disease incidence by the standard synthetic fungicide, Thiram, and confirms the efficacy of the crude extract. Although covered kernel smut incidence is relatively low (9%) compared to that of loose smut incidence (25%) in the untreated controls, all (100%) plants grown from inoculated seeds can be totally protected against infection by covered kernel smut while the incidence of loose smut is significantly reduced following seed treatment with the aerial part crude extract of *T. violacea*. The significant differences in grain yield obtained between plants grown from treated and untreated seeds confirm the impact that both diseases have on yield as well as the efficacy of the crude extract in controlling both diseases.

Treatment of sorghum seeds with an aerial part crude extract of *T. violacea* has no apparent inhibitory effect on either seed germination or seedling growth. The latter, together with the significant in vitro and in vivo antifungal activities demonstrated in this study for an aerial part crude *T. violacea* extract against a broad spectrum of fungal pathogens, confirms both its application potential and reliability.

In general, although the synthetic fungicide, Thiram, is very effective in controlling covered kernel and loose smuts infection in sorghum, the application of crude plant extracts including *T. violacea* seems a convenient, effective and economical alternative to the majority of subsistence farmers who cannot afford synthetic chemicals.

(6) The Effect of *Tulbaghia* on the Defense Mechanism of Plants (SAR)

Plants (e.g. wheat and sunflower) elicit, when treated with an extract of *Tulbaghia violacea* and another reference plant (*A. africanus*) according to the invention, a significant activation of PR-proteins such as NADPH oxidase, peroxidase and β-1,3-glucanse.

Figure 9:
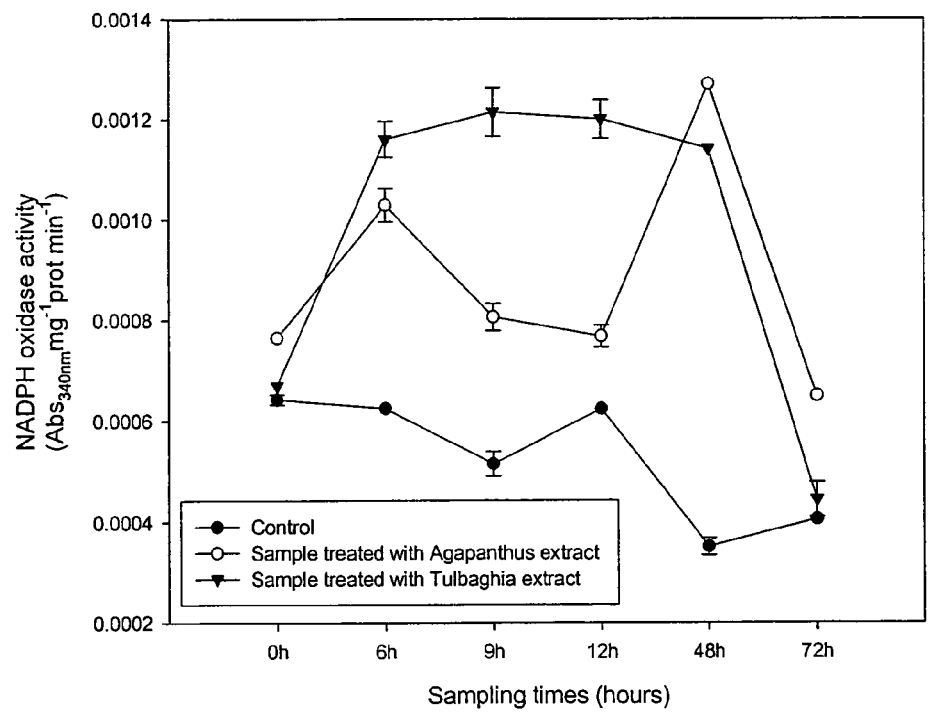
Figure 10:
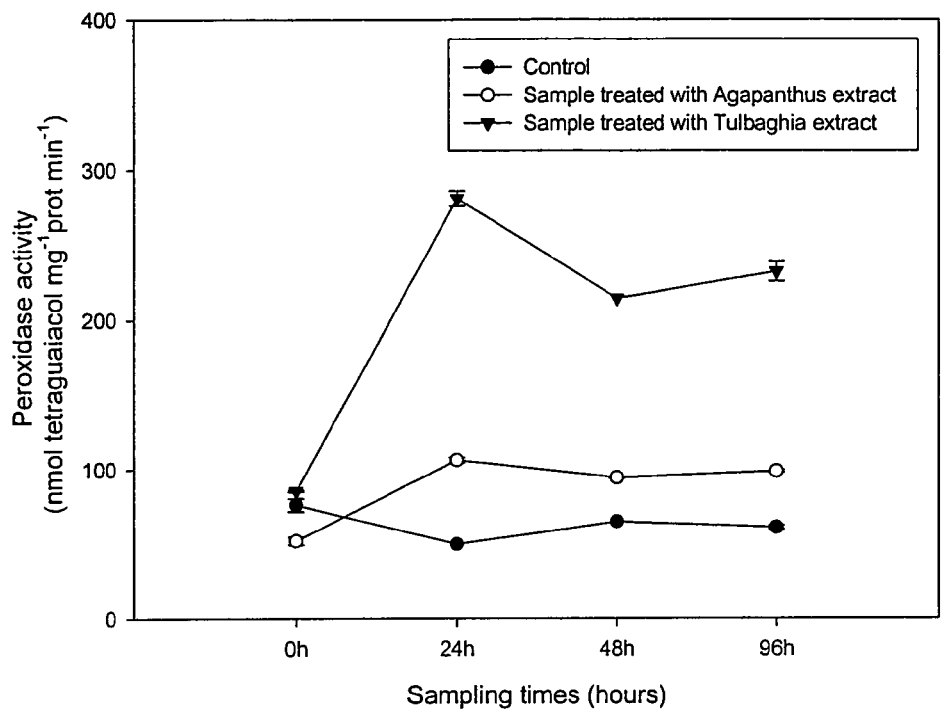
Figure 11:
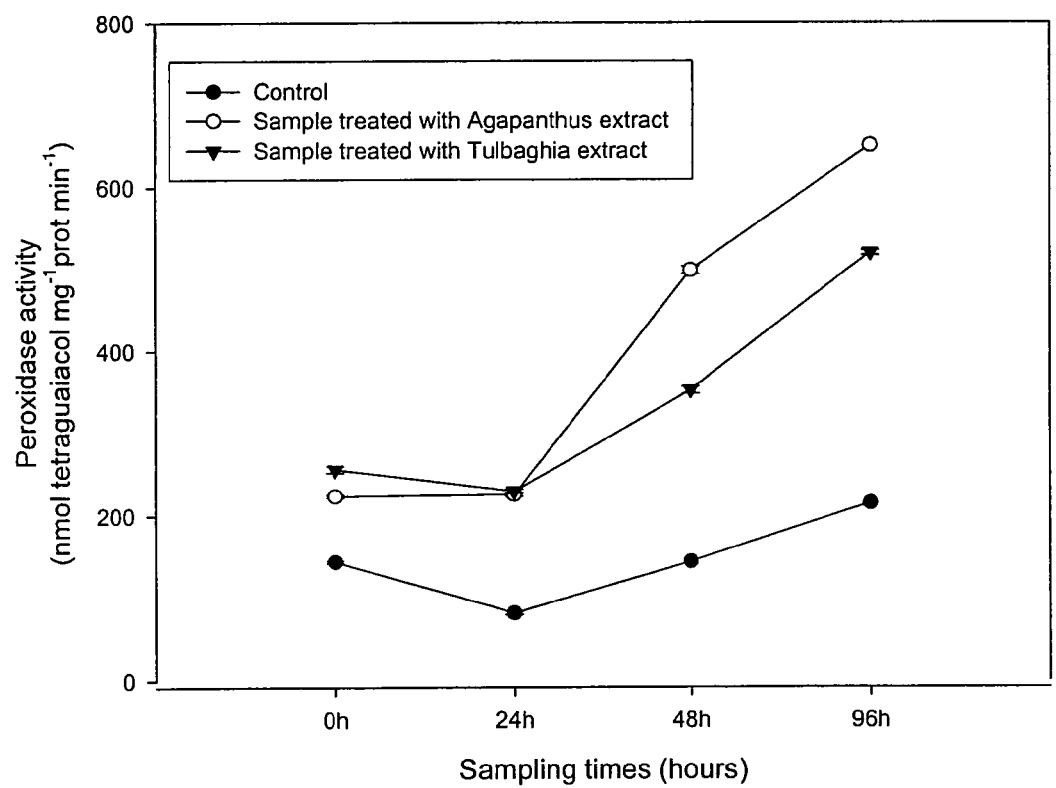

Wheat plants treated with the *T. violacea* extract exhibit two peaks in NADPH oxidase activity. The first peak is reached 6 h after treatment with an induced increase in activity of 36% over the previous sampling time compared to the untreated control. The second much higher peak is reached at 12 h after treatment with an induced increase in activity of 100% over the previous sampling time (FIG. 8) after which the activity declines. Sunflower treated with the *T. violacea* extract exhibits an increase in NADPH oxidase activity of 88.5% during the first 6 h after treatment. This elevated level of activity is maintained for 48 h after treatment followed by a sharp decline up to 96 h after treatment (FIG. 9). Treatment of wheat with the *T. violacea* extract results in an enormous induction in peroxidase activity of 460% after 24 h. This activity also remains high over the test period (FIG. 10). In the case of sunflower the *T. violacea* extracts induce peroxidase activity significantly especially after 48 h and 96 h (FIG. 11). For *T. violacea* the induction was 112% after 48 h and 150% after 96 h. The sunflower control, however, showed a slight increase in peroxidase activity over the 96 h period indicating some natural resistance. *Tulbaghia* extracts induce defense mechanisms in wheat and sunflower plants. These extracts induce localized acquired resistance, the accumulation of PR-proteins by gene activation and ultimately systematic acquired resistance. The fact that the extracts induce a defense response in both the wheat and sunflower samples indicate that the extracts are responsible for the induction of a general broad-spectrum defense response. The extract-induced increase in defense related enzyme activities was lower, but comparable to the increase obtained during infection with resistant cultivars (F) Isolation, Purification and Identification of Antifungal Compounds from Soil and Aerial Plant Part Extracts of *Tulbaghia violacea*

(1) Recovery of Liquid-Liquid Semi-Purified Extracts from the Crude Methanol Extract Most of the compounds in both the aerial and below soil part extracts are more soluble in hexane than in the more polar solvents used. As much as 9.20 g (14.6%) of compounds from the aerial plant parts and 7.43 g (8.4%) from the below soil parts can be recovered in hexane compared to the much lower recovery in the more polar solvents (Table 9).

TABLE 9

Recovery of compounds from *Tulbaghia violacea* by solvents in order of increasing DC-values using a liquid-liquid extraction procedure

| Organic solvent | Aerial part extract | | Below soil part extract | |
|---|---|---|---|---|
| | Mass (g) | % Recovery | Mass (g) | % Recovery |
| Hexane | 9.20 | 14.6 | 7.43 | 8.4 |
| Diethyl ether | 1.57 | 2.5 | 1.74 | 1.9 |
| Ethyl acetate | 0.56 | 0.9 | 1.07 | 1.2 |
| Dichloromethane | 0.10 | 0.1 | 0.12 | 0.14 |

(2) Antimicrobial Properties of the Liquid-Liquid Aerial and Below Soil Part Extracts of *T. violacea*

Figure 6:
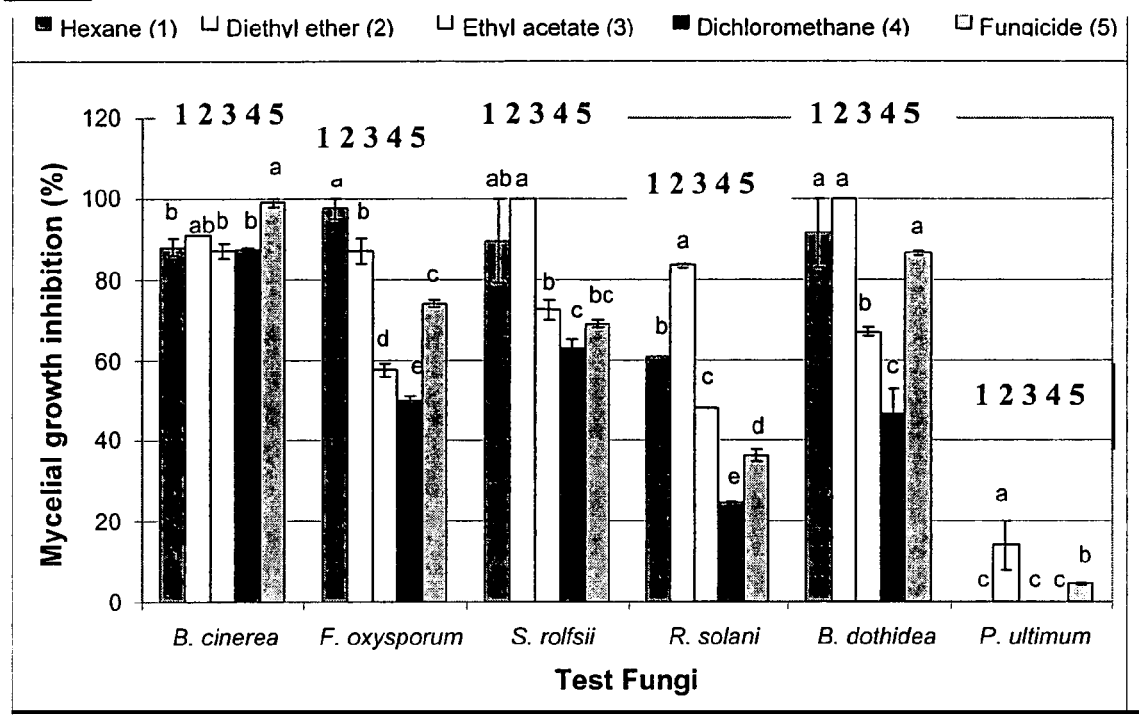

Although all of the liquid-liquid extractions from the aerial parts of *T. violacea* show antifungal activity against most of the test organisms to a greater or lesser extent, that of the hexane and diethyl ether extracts are significantly ($P<0.05$) higher (FIG. 6). Mycelial growth inhibition of all test fungi by one or both the hexane and diethyl ether extracts are higher than 80% except in the case of *P. ultimum*, well known for its resistance against fungicides, as well as *R. solani* (61%). Both these extracts compare favourably with the standard fungicide used as a positive control. Antifungal compounds in the below soil parts (FIG. 7) of *T. violacea* show the same tendency to accumulate in the hexane and diethyl ether fractions after liquid-liquid extraction as was the case with the aerial parts (FIG. 6). However, in the case of *B. dothidea*, all of the extracts show exceptionally high antifungal activity.

(3) Column Chromatography Fractionation (CCF) of the Most Active Hexane Extracts Only compounds in the active hexane liquid-liquid extraction can be purified further by means of column chromatography in the case of both the aerial and below soil parts of *T. violacea*. The reason for this decision is the fact that six times more compounds can be retrieved from the hexane extract compared to the diethyl ether active extract in the case of the aerial parts and four times more in the case of the below soil parts. More than 1500 column chromatography fractions can be obtained from the hexane extracts for each of the aerial and below soil parts. After these can be subjected to Q-TLC, those fractions with similar profiles are combined. Twenty eight combined column fractions can be obtained for the aerial parts and 20 for the below soil parts in this manner. The results are shown in Table 10. Only four combined column fractions ($A_5$, $A_6$, $A_7$ and $A_8$) from the aerial parts display above average antifungal activity (100, 95, 52.6 and 60.5%) respectively, while only two combined fractions ($B_2$ and $B_3$) from the below soil parts are active (87 and 97% respectively). The rest of the fractions fail to suppress mycelial growth of *F. oxysporum* effectively (Table 10). Only combined column fractions that show more than 50% mycelial growth inhibition of the test fungus on average can be purified further by means of preparative thin layer chromatography (P-TLC). The reason for taking 50% inhibition as criterion is to compensate for the possibility that active substances could act synergistically and that, on separation, activity can decline.

TABLE 10

Percentage (%) mycelial growth inhibition of the test organism, *Fusarium oxysporum*, by combined column chromatography fractions of aerial and below soil part extractions of *T. violacea*. (B = below soil parts and A = aerial parts).

| Fraction number from A | Mass (mg) recovered | % Mycelial growth inhibition by compounds from A | Fraction number from B | Mass (mg) recovered | % Mycelial growth Inhibition by compounds from B |
|---|---|---|---|---|---|
| 1 | 19.9 | 1.5 | 1 | 147.4 | 24.0 |
| 2 | 28.9 | 11.7 | $B_2$/2 | 411.1 | 87.0 |
| 3 | 105.8 | 11.7 | $B_3$/3 | 109.8 | 97.0 |
| 4 | 97.9 | 25.9 | 4 | 947.3 | 12.0 |
| $A_5$/5 | 316.5 | 100.0 | 5 | 10.7 | 12.7 |
| $A_6$/6 | 460.7 | 95.0 | 6 | 17.7 | 11.6 |
| $A_7$/7 | 430.6 | 52.6 | 7 | 22.7 | 12.4 |
| $A_8$/8 | 353.5 | 60.5 | 8 | 26.1 | 12.0 |
| 9 | 120.4 | 34.7 | 9 | 3.1 | 11.9 |
| 10 | 121.3 | 0.3 | 10 | 33.6 | 20.0 |
| 11 | 426.0 | 10.9 | 11 | 155.8 | 9.6 |
| 12 | 848.4 | −10.3* | 12 | 24.3 | 14.3 |
| 13 | 53.9 | −1.4* | 13 | 478.0 | 3.5 |
| 14 | 210.2 | −3.3* | 14 | 590.2 | 27.5 |
| 15 | 59.3 | 5.8 | 15 | 73.8 | 16.5 |
| 16 | 294.7 | 1.6 | 16 | 197.1 | 27.8 |
| 17 | 288.7 | 30.1 | 17 | 114.4 | 11.7 |
| 18 | 196.9 | 40.5 | 18 | 213.6 | 34.8 |
| 19 | 218.0 | 8.2 | 19 | 110.3 | 19 |
| 20 | 78.1 | 15.8 | 20 | 447.2 | 37.9 |
| 21-28 | 2201.5 | −23.4* | | | |
| Fungicide | | 78.0 | | | 78.0 |
| Control | | 0 | | | 0 |

Values with negative (−) values indicate mycelial growth stimulation.
Only the six active combined column chromatography fractions shown in Table 10 ($A_5$, $A_6$, $A_7$, $A_8$, $B_2$ and $B_3$) are subjected to further purification by means of P-TLC.

(4) Activity Directed Preparative Thin Layer Chromatography (P-TLC) Purification of Active Combined Column Chromatography Fractions Activity directed purification of compounds in the six combined column fractions are done by means of P-TLC produced four compounds ($A_{5.2}$, $A_{6.1}$, $A_{7.1}$ and $A_{7.2}$) from the aerial part fractions that show antifungal activity higher than 50% (100, 85, 87 and 50% respectively) and two ($B_{2.2}$ and $B_{3.2}$) from the below soil part fractions (87 and 72% respectively; Table 11). These six compounds are identified and their chemical structures can be elucidated by means of nuclear magnetic resonance (NMR) spectroscopy. Interestingly, on separation, compounds in column chromatography fraction 8 ($A_8$) of the aerial parts, that showed 60.5% mycelial growth inhibition (Table 10) when together in semi-purified form, lose their antifungal activity after P-TLC purification (Table 11).

TABLE 11

Percentage (%) mycelial growth inhibition of *F. oxysporum* by different compounds of *T. violacea* after P-TLC separation

| Aerial compd. no | Mass (mg) | % inhibition | Below soil compd. no. | Mass (mg) | % inhibition |
|---|---|---|---|---|---|
| $A_{5.1}$ | 94.9 | 0 | $B_{2.1}$ | 26.2 | 0 |
| $A_{5.2}$ | 44.1 | 100 | $B_{2.2}$ | 110.3 | 87 |
| $A_{6.1}$ | 25.3 | 85 | $B_{3.2}$ | 15.8 | 72 |
| $A_{6.2}$ | 34.1 | 48 | $B_{3.3}$ | 5.9 | 0 |
| $A_{6.3}$ | 10.5 | 37 | | | |
| $A_{7.1}$ | 9.3 | 87 | | | |
| $A_{7.2}$ | 24.5 | 52 | | | |
| $A_{8.1}$ | 7.1 | 0 | | | |
| $A_{8.2}$ | 6.2 | 5 | | | |
| $A_{8.3}$ | 9.1 | 0 | | | |

(5) Identification of Active Compounds Purified from the Extracts of Aerial and Below Soil Parts of *T. violacea* by Nuclear Magnetic Resonance (NMR) Spectroscopy and Mass Spectrometry In order to obtain an acceptable level of purity, the complex semi-purified hexane extracts of aerial and below soil parts of *T. violacea* are subjected to chromatographic fractionation which was followed by P-TLC separation. Fractionation of the hexane extract by silica column chromatography with hexane-acetone (95:5) as the eluant at a flow rate of 30 ml/h, followed by several P-TLC purifications in hexane-acetone (9.5:0.5), results in 6 fairly pure fractions (see above). Bioassay on the fractions reveals that only two fractions from the below soil parts and four from the aerial parts show promising results relevant to this investigation.

The presence of glycerol trilinoleate in all the fractions hampers separation and renders structural elucidation difficult. Further purification of the fractions by P-TLC affords fairly pure compounds ($B_{2.2}$ and $B_{3.2}$ from the below soil parts and $A_{5.2}$, $A_{6.1}$, $A_{7.1}$ and $A_{7.2}$ from the aerial parts) whose structures can be determined by standard NMR spectroscopic methods and Mass spectrometry. A strong garlic aroma suggests the compounds to belong to the thiol (mercaptan) class. Absence of the aromatic and alkenoid protons (between δ 5-8) in the $^1$H NMR spectra of all the compounds eliminate the aromatic character in their structures. However, simple $^1$H NMR spectra of all the compounds display only singlet peaks resonating between δ 2.0 and 4.5. All the corresponding $^{13}$C NMR spectra of all the compounds show no resonance above 45 ppm, further eliminating the C=S and C=O bond characters in the structures. These findings narrow the possibilities of the compounds to belong to either the thio or oxo aliphatic class. Further evaluation of the $^{13}$C NMR spectra show the most de-shielded signal to appear at ~45 ppm which is characteristic of the thio-bond (C—S).

The following six compounds with antifungal activity have been found and identified according to this invention:

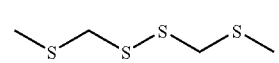

Compound (1)

Empirical formula: $^1CH_3S^3CH_2SS^6CH_2S^8CH_3$ 2,4,5,7-Tetrathiaoctane

Compound (1) or $B_{2.2}$ can be isolated from the impure column fraction $B_2$ by means of P-TLC purification (Hexane:Acetone: 9.5:0.5) as a yellow oil. The $^1$H NMR spectrum of compound (1) show a singlet at $\delta_H$ 4.00 ($\delta_C$ 45.2 ppm), integrating for 4 protons, and a singlet at $\delta_H$ 2.21 ($\delta_C$ 17.3 ppm), integrating for 6 protons, suggesting a thiomethylene and two thiomethyl groups. The methylene protons at $\delta_H$ 4.00 and the methyl protons at $\delta_H$ 2.11 are consistent with the presence of the $CH_2$—S and $CH_3$—S groups, respectively. Electron ionization mass spectroscopy (EIMS) of (1) show the base peak at m/z 186, consistent with the molecular formula $C_4H_{10}S_4$, and this was in agreement with the suggested structure (1), a compound previously isolated by Burton and Kaye (1992).

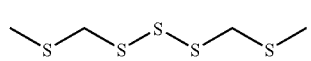

Compound (2)

Empirical formula: $^1CH_3S^3CH_2SSS^7CH_2S^9CH_3$ 2,4,5,6,8-Pentathianonane

Following P-TLC separation (Hexane:Acetone: 9.5:0.5), compound (2) or $B_{3.2}$ can be isolated as a yellow oil from combined column fraction $B_3$. In the $^1$H NMR spectrum of compound (2) (Plate 6.3) only two singlets at $\delta_H$ 4.15 and $\delta_H$ 2.29, integrating for 2 protons and 6 protons, respectively, can be observed. The $^1$H NMR data of (2) is very similar to that of (1) suggesting a very similar structure. The integrals of the peaks suggested the presence of two thiomethylene and two thiomethyl groups. Assignment of structure (2) is based on comparison of the chemical shifts of the protons in the $^1$H NMR spectra of compounds (1 and 2). The more de-shielded protons in the $^1$H NMR spectrum of (2) require additional sulphur atoms in the structure.

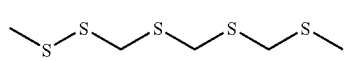

Compound (3)

Empirical formula: $^1CH_3SS^4CH_2S^6CH_2S^8CH_2S^{10}CH_3$ 2,3,5,7,8-Pentathiadecane Purification of fraction $A_5$ by P-TLC (Hexane:Acetone: 9.5:0.5) affords compound (3) or $A_{5.2}$ as a yellow oil that shows similarity to compounds (1 and 2), The $^1$H NMR spectrum of compound (3), exhibits three methylene protons around $\delta_H$ 4.00 and two methyl protons around $\delta_H$ 2.00 consistent with the presence of $CH_2$—S and $CH_3$—S groups, respectively. Resonances of the peaks in the $^{13}$C NMR spectrum is in agreement with the corresponding peaks of the $^1$H NMR spectrum. The singlets at $\delta_H$ 3.8 ($\delta_C$ 37.2 ppm), $\delta_H$ 3.95 ($\delta_C$ 40.9 ppm) and $\delta_H$ 4.11 ($\delta_C$ 45.5 ppm) are assigned to H-8, H-6, and H-4, respectively. The methyl protons were observed at $\delta_H$ 2.18 ($\delta_C$ 15.0 ppm), H-10 and 2.25 ($\delta_C$ 15.6 ppm), H-1. Electron ionization mass spectroscopy (EIMS) show [M$^+$] at m/z 232 consistent with the molecular formula $C_5H_{12}S_5$ and this is in agreement with the suggested structure of compound (3).

Compound (4)

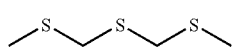

Empirical formula: $^1CH_3S^3CH_2S^5CH_2S^7CH_3$ 2,4,6-Trithiaheptane

Attempts to purify compound $A_{6.1}$ to yield compound (4) were unsuccessful. The $^1$H NMR spectrum of compound (4) show two methylene singlets and one methyl singlet corresponding to the $^{13}$C NMR spectrum. In comparison to the $^1$H NMR spectrum of compound (1), this indicates a mixture of compounds (4) and (1) in almost equal amounts. Furthermore it is observed that the $^1$H NMR spectrum of compound (4), the methylene proton ($\delta_H$ 4.5) is de-shielded in comparison to that in compound (1) due to an extra sulphur atom in the structure of (1). When the methylene protons ($\delta_H$ 4.00) and the methyl protons ($\delta_H$ 2.21) of compound (1) are eliminated from the spectrum, the remaining protons can be allocated to compound (4).

Compound (5)

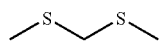

Empirical formula: $^1CH_3S^3CH_2S^5CH_3$ 2,4-Dithiapentane

P-TLC isolation of compound $A_{7.1}$ from fraction $A_7$ (Hexane:Acetone: 9.5:0.5), affords compound (5) as a yellow oil. Methylene and methyl protons resonating as singlets at $\delta_H$ 3.67 and 2.18, respectively, are observed in the $^1$H NMR spectrum. The less de-shielded CH$_2$—S methylene ($\delta$ 3.67), as compared to the CH$_2$—SS integrating for 2 protons, and the characteristic CH$_3$—S methyl protons integrating for six protons, can be assigned to H-2 and H-1, respectively.

Compound (6)

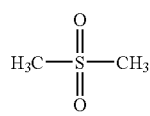

Empirical formula: $CH_3SO_2CH_3$

Methylthiosulphonate

P-TLC separation (Hexane:Acetone: 9.5:0.5) of compound 6 ($A_{7.2}$) from fraction $A_7$ is also a yellow oil. Although the $^1$H NMR spectrum of compound (6) shows peaks which belonged to linoleic acid, a prominent singlet at $\delta$ 3.7 that is not part of those peaks observed. Owing to the impurity of the isolated compound, accurate mass could not be determined. The assignment of the tentative structure (6) is based entirely on the resonating position of the methyl protons in the $^1$H NMR spectrum. The electronegative sulphur and oxygen atoms de-shield the —CH$_3$ protons shifting them to chemical shift $\delta$ 3.7 as opposed to CH$_3$S protons which resonate around $\delta$ 2.10.

(6) Discussion

In this study, the liquid-liquid extraction procedure of aerial and below soil parts of *T. violaceae* show that hexane extracts substantially more compounds than do the other organic solvents diethyl ether, ethyl acetate and dichloromethane indicating that the plant contains a large amount of rather non-polar substances. This can be confirmed by both mass recovery measurement and qualitative thin layer chromatography (Q-TLC) profiles of the liquid-liquid extracts. Although six times less compounds can be recovered from the diethyl ether extract of the aerial parts and four times less from the below soil part extract compared to hexane, diethyl ether extracts the second most compounds. Much less compounds can be recovered from the remaining more polar solvents, ethyl acetate and dichloromethane.

The subsequent bio-test for antifungal activity confirms that most of the active substances are contained in the hexane and diethyl ether extracts as both show higher activity against all six test fungi. However, albeit much lower, the ethyl acetate and dichloromethane liquid-liquid extracts also show antifungal activity to some extent indicating that the active principles seemed to have been either thinly distributed between organic solvents or that other, more polar, substances are also active. For some fungi (e.g. *B. cinerea, S. rolfsii* and *B. dothidea*) there are no significant difference in mycelial growth inhibition between the hexane and diethyl ether extracts of both aerial and below soil part extracts. As substantially more compounds can be recovered from the hexane extract, and diethyl ether also being rather non-polar, it is speculated that the active principles contained in these two solvents are probably the same. Activity directed column chromatography separation of compounds in the hexane extracts yields four active combined fractions from the aerial part and two from the below soil part extracts. Subsequent activity directed purification of compounds from these column fractions by means of P-TLC results in the isolation of six pure compounds that all show above average antifungal activity. By means of NMR spectroscopy their chemical structures can be elucidated and the compounds identified. From the below soil parts of *T. violacea* two antifungal compounds can be identified as the known 2,4,5,7-tetrathiaoctane and the novel 2,4,5,6,8-pentathianonane. From the aerial parts four antifungal compounds can be identified. Of these, only methyl thiosulphonate is known while 2,3,5,7,8-pentathiadecane, 2,4,6-trithiaheptane and 2,4-dithiapentane are most probably novel compounds. What is surprising is the fact that all of the antifungal compounds purified form the hexane extracts of aerial and below soil parts of *T. violacea*, except for methylthiosulphonate, are rather simple aliphatic sulphur-containing alkanes.

Finally, an aspect that needs special consideration is the fact that the methanolic crude extract of *T. violacea* shows higher broad spectrum antifungal activity against all the test fungi than did the liquid-liquid extracts and the semi-purified column chromatography fractions. Further, one of the active semi-purified column chromatography fractions ($A_8$ of the aerial parts) shows high antifungal activity but on separation of the compounds contained in this fraction, the activity was lost. This complicates the isolation and identification of all active substances from plants and strongly indicates that the natural resistance of plants against biotic stress conditions largely depends on the synergistic or combined effect of different active compounds. The known presence of polar saponins and flavonoids in *T. violaceae* that are anti-infective agents (Pretorius, 2003, *Current Medicinal Chemistry: Anti-infective Agents* 2:335-353.), in combination with the presence of active sulphur containing compounds identified according to this invention, can explain the higher antifungal activity detected in the crude and semi-purified extracts compared to that of purified compounds.

FIGURE LEGENDS

FIG. 1: Percentage (%) in vitro growth inhibition of plant pathogenic fungi by fresh crude methanol extracts of *T. violacea* at a concentration of 1 g/l. Bars designated with different letters for each fungus differed significantly (P<0.05) according to Tukey's Mean Significant Difference (MSD) statistical procedure. Y-axis: mycelial growth inhibition (%). 1=aerial part; 2=below soil part; 3=fungizide FIG. 2: Percentage (%) in vivo growth inhibition of plant pathogenic fungi by fresh crude methanol extracts of *T. violacea* at a concentration of 1 g/1 after storage at −20° C. for one year. Bars designated with different letters for each fungus differed significantly (P<0.05) according to Tukey's Mean Significant Difference (MSD) statistical procedure. Y-Axis: mycelial growth inhibition (%). 1=aerial part; 2=below soil part; 3=fungizide FIG. 3: The effect of crude aerial and below soil part extracts of *T. violacea* on the respiration rate of a monoculture yeast cells at 30 minute intervals over a three-hour period. ComCat® and distilled water served as controls. X-axis: time (min); Y-axis: CO2 release ($cm^3$).

FIG. 4: The effect of crude aerial and below soil part extracts of *T. violacea* on radicle growth of Cress seedlings at 24 hour intervals over a 96-hour incubation period. ComCat® and distilled water served as controls. X-axis: time (h); Y-axis: radicle growth (mm).

FIG. 5: The effect of crude aerial and below soil part extracts of *T. violacea* on coleoptile growth of Cress seedlings at 24 hour intervals over a 96-hour incubation period. ComCat® and distilled water served as controls. X-axis: time (h); Y-axis: coleoptile growth (mm).

FIG. 6: Percentage (%) in vitro mycelial growth inhibition of plant pathogenic fungi by semi-purified aerial part extracts of *T. violacea* at a concentration of 1 g/l. Bars designated with different letters for each test fungus differed significantly (P<0.05) according to Tukey's Mean Difference (MSD) procedure. Y-axis: mycelial growth inhibition (%). 1=hexane, 2=diethyl ether, 3=ethyl acetate, 4=dichloromethane, 5=fungizide.

Figure 7:
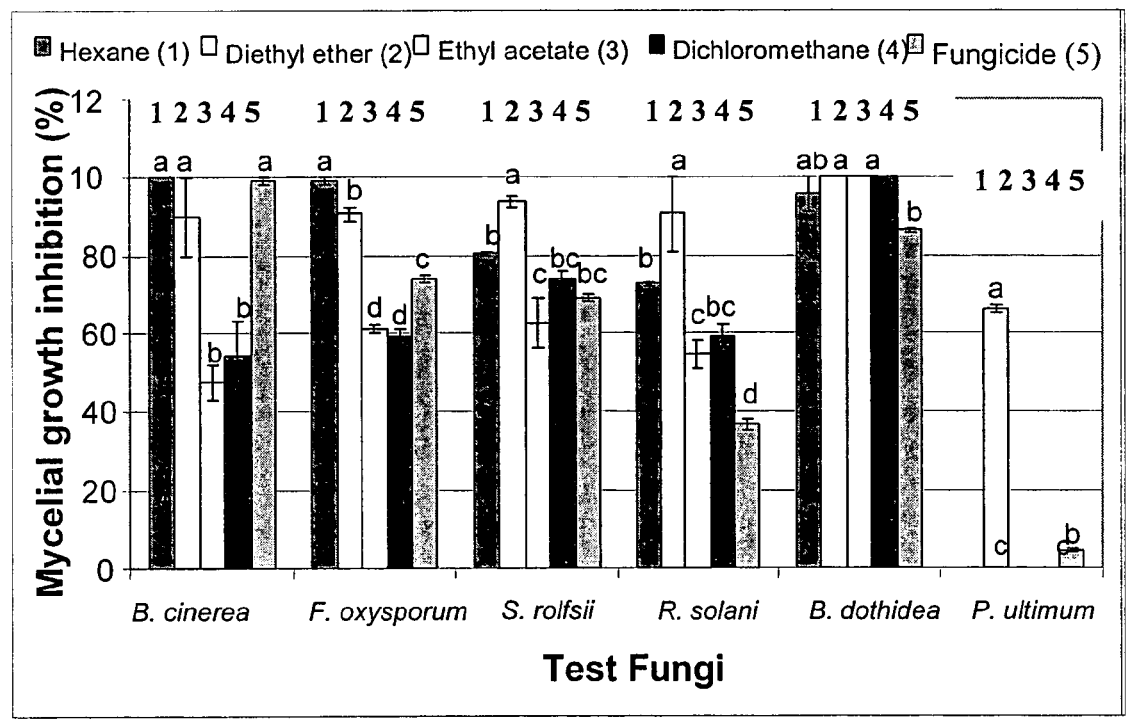

FIG. 7: Percentage (%) in vitro mycelial growth inhibition of plant pathogenic fungi by semi-purified below soil part extracts of *T. violacea* at a concentration of 1 g/l. Bars designated with different letters for each test fungus differed significantly (P<0.05) according to Tukey's Mean Difference (MSD) procedure. Y-axis: mycelial growth inhibition (%). 1=hexane, 2=diethyl ether, 3=ethyl acetate, 4=dichloromethane, 5=fungizide.

Figure 8:
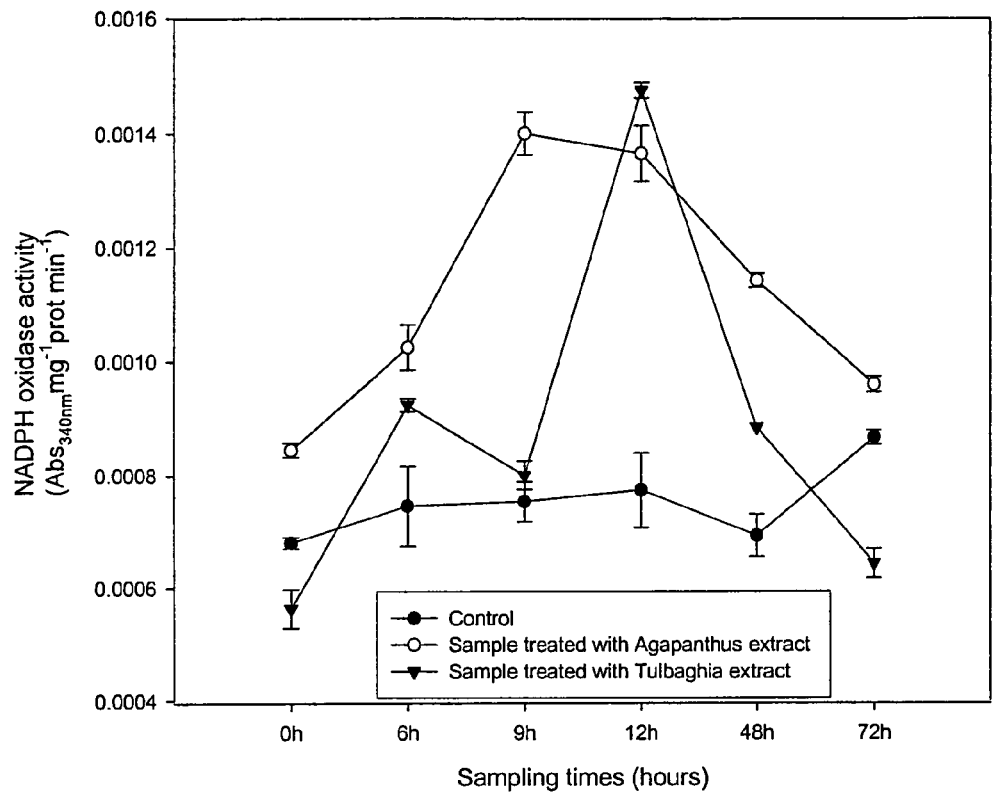

FIG. 8: NADPH oxidase activity pattern in wheat treated with a *Tulbaghia* extract and an *Agapanthus* extract (as reference) according to the invention in dependency of the time after treatment.

FIG. 9: NADPH oxidase activity pattern in sunflower treated with an *Tulbaghia* extract and an *Agapanthus* extract (as reference) according to the invention in dependency of the time after treatment.

FIG. 10: peroxidase activity pattern in wheat treated with an *Tulbaghia* extract and an *Agapanthus* extract (as reference) according to the invention in dependency of the time after treatment.

FIG. 11: peroxidase activity pattern in sunflower treated with an *Tulbaghia* extract and an *Agapanthus* extract (as reference) according to the invention in dependency of the time after treatment.

EXAMPLES

Analysis of variance (ANOVA) in the below-outlined examples was performed on the data, using the NCSS 2000 Statistical program, to identify differences between treatments. Tukey's mean significant difference (MSD) procedure for comparison of means (Steele and Torrie, 1980, *Principles and procedures of statistics, $2^{nd}$ Edition*. New York: McGraw-Hill.) was applied to separate means (P<0.05)).

Example 1

Plant Material

Whole *Tulbaghia violacea* plants were initially collected from the Blyde River Canyon Nature Reserve (BRC) South Africa. The taxonomic identification of the species was performed by a taxonomist from the National museum, Bloemfontein, South Africa. A voucher specimen was processed according to standard procedures and deposited in the herbarium of the museum. Bulk samples of the species were later collected from the Botanical Gardens, Bloemfontein between January and March 2001, 2002 and 2003.

Example 2

Preparation of the Plant Material

Health and laboratory safety standards were followed in the handling of the unknown material as it was assumed to be dangerous. Plant material was examined beforehand for any form of infection or insect damage and such infected material was not used. Plants were divided into (a) aerial parts (stems and leaves) and (b) below soil parts (rhizome and roots). After the fresh mass of the different plant parts was determined, the plant material was dried in an oven for two weeks at 35° C. and the dry mass determined. Subsequently, dried plant material was ground, using a Retsch SM 2000 cutting mill and the dry mass determined again. After grinding, small representative amounts of each sample were transferred into plastic Ziploc bags, sealed and stored in a freezer at −20° C. until crude extracts were prepared. Percent loss during grinding was calculated as follows:

$$\text{Percent loss at grinding} = \frac{(\text{net mass of dry sample}) - (\text{net mass of ground sample}) \times 100}{(\text{net mass of dry sample})}$$

Example 3

Preparation of Crude Extracts

The two ground samples (aerial and below soil parts) were transferred into separate 5-litre Qorpak jars labelled and covered with 100% methanol at a ratio of two ml g$^{-1}$ dry weight. The lids were closed firmly, sealed with parafilm to prevent leakage and placed on a roller mill for 24 hours. Extraction was performed twice by replacing the methanol. Subsequently, each sample was filtered twice, first under vacuum through a double layer of Whatman filter paper (No. 3 and No. 1) using a Buchner funnel and then by gravity through a single sheet of Whatman No. 1 filter paper. Most of the methanol was removed from the extracts by means of vacuum distillation at 35-40° C. using a Büchi Rotary Evaporator. On the following day the same procedure was followed with the re-extracted plant material. Final filtrates from the twice extracted plant material were combined and concentrated to dryness under vacuum by means of a Speedvac Concentrator at −140° C. for 24 hours. After determining the dry matter yields, the crude aerial and below soil parts were stored separately at −20° C. for later use.

Example 4

Screening Crude Methanol Extracts of *T. violacea* for Antibacterial Activity (a) Preparation of Bacteria Mother Cultures Antibacterial activity was qualitatively evaluated by means of the agar plate diffusion assay technique (Rios et al., 1988, *Journal of Ethnopharmacology* 23:127-149). Plate count agar (PCA) was used to prepare mother cultures of the following six plant pathogens and one human bacterium in advance: *Clavibacter michiganense* pv. *michiganense*, *Pseudomonas syringae* pv *syringae*, *Erwinia carotovora* subsp *carotovora*, *Agrobacterium tumefaciens*, *Ralstonia solanacearum*, *Xanthomonas campestris* pv *phaseoli*, all plant pathogens, as well as *Moraxella catharrhalis* (MC) a human pathogen. Two stock cultures were prepared for each bacterium of which one was a working culture and the other a back-up culture. Cultures were stored at 5-15° C., except for *Moraxella* that was stored at 4° C.

From the bacteria mother cultures, seven nutrient agar (NA) plates were separately inoculated with the seven bacteria two days prior to the anti-bacterial bioassay. These were incubated at 25° C., except for the *Moraxella* plate which was incubated at 35° C. one day prior to bioassay in order to obtain pure line colonies. All cultures were checked for contamination. After two days, the uncontaminated pure colonies of the 2-day old bacteria cultures were transferred from the agar plates into seven labelled test tubes containing sterilized distilled water, in the case of the plant pathogens, and sterilized saline water in the case of *Moraxella*. Diluted bacteria suspensions were compared to the McFarland standard in order to obtain the required concentration of 1×10$^6$ CFUs (colony forming units) per ml.

(b) Antibacterial Bioassay

Five grams nutrient agar was dissolved in 200 ml distilled water, autoclaved at 121° C. for 20 minutes and transferred into seven Petri-dishes to cool and set. The crude extracts were assayed as aqueous suspensions in 10% (v/v) DMSO (dimethyl sulphoxide) at a concentration of 50 mg ml$^{-1}$ by transferring a maximum of 40 µl into 5 mm holes made in the agar with a sterile cork borer. All activities were carried out in a pre-sterilized laminar flow cabinet to avoid contamination. Each test plate was divided into five parts and the extracts as well as the 10% (v/v) DMSO solution (positive control) transferred into the holes in the agar. Plates were left for 20 minutes to allow the extracts and DMSO to diffuse into the agar and subsequently incubated at 25° C. (plant pathogens) or 35° C. (Moraxella) for three days. Each plate was inoculated with the different bacterial suspensions using sterile swabs and spread evenly over the plate. After three days, the zones of inhibition were measured using a digital calliper, excluding the hole (Heisey and Gorham, 1992), and used as a qualitative indicator for antibacterial activity.

Example 5

Screening Crude Methanol Extracts of *T. violacea* for Antifungal Activity

A modified agar dilution method (Rios et al., 1988, l.c.) was used for determining the mycelial growth inhibition of the test organisms by the crude extracts.
(a) Preparation of fungus mother cultures.

Two percent malt extract agar (4 g Malt extract; Difco, 2.8 g Technical agar; Difco) was prepared in 200 ml distilled water and autoclaved for 20 minutes at 121° C. Subsequently, the media was cooled in a water bath at 45° C. and 60 µl of a 33% (m/v) Streptomycin solution added to the basal medium for controlling bacterial growth. The agar medium was then transferred to Petri dishes and allowed to set. Two mother cultures for each fungus were prepared for the following six plant pathogenic fungi: *Botrytis cinerea*, *Fusarium oxysporum*, *Sclerotium rolfsii*, *Rhizoctonia solani*, *Botryosphaeria dothidea* and *Pythium ultimum*. An inoculum of each fungus was placed face down on the agar media in separate Petri dishes (two replications) and incubated at 25° C. for 8 to 10 days. Subsequently, 12 glass culture bottles were half filled with distilled water and autoclaved for 20 minutes at 121° C. Pieces of agar containing the organisms from a pair of Petri dishes (two replications per fungus) were then transferred to the autoclaved culture bottles, sealed with parafilm and stored at 4° C., except for *Rhizoctonia solani* and *Pythium ultimum* that were stored at 25° C.
(b) Bioassay Two percent malt extract agar (MEA) was prepared as described for the preparation of mother cultures. Each extract was dissolved in 100 ml sterile distilled water and amended in the agar to yield a final concentration of 1 mg/ml (1 g/l). The medium, also containing 33% Streptomycin, was transferred to 90 mm sterile plastic Petri dishes and left to set. The centre of each test plate was subsequently inoculated with a 5 mm size plug, for each of the pathogens separately, and incubated for three days at 25±2° C. in a growth cabinet. Radial mycelial growth was determined after three days by calculating the mean of two perpendicular colony diameters on each replicate (three replicates per organism). An inoculated plate for each pathogen, containing only the basal medium, served as control. The means of the two measurements were used to calculate percent (%) inhibition:

$$MEA \text{ mean(control)} = \frac{X+Y}{2}, \text{EXTRACT mean} = \frac{A+B}{2}$$

$$\text{Percent inhibition} = \frac{(MEA \text{ mean} - 5) - (EXTRACT \text{ mean} - 5)}{(MEA \text{ mean} - 5)} \times 100$$

Additionally, a plate containing 1 µg/ml Carbendazim/difenoconazole (Eria®-187.5 g L$^{-1}$ EC) was used as standard fungicide against each test organism separately to determine the effectiveness (expressed as % inhibition) of the extracts by comparison. Each treatment was performed in triplicate.

Example 6

Screening Crude Methanol Extracts of *T. violacea* for Biostimulatory Activity Two methods were applied to determine the biostimulatory potential of the organ crude extracts of *T. violacea*:
Method 1: Manometric Method to Determine the Effect of the Crude Extracts on the Respiration Rate of a Monoculture Yeast Cells.

A specially constructed glass respirometer with a short bulged section (reservoir) to contain the yeast cells and a long calibrated tube, closed at the top end to collect $CO_2$ gas, was used to determine the effect of the crude organ extracts (aerial and below soil parts) of *T. violacea* on the respiration rate of yeast cells. Dry baker's yeast (0.8 g) was placed in the reservoir of the respirometer. Subsequently, 70 ml of each of the organ extracts previously prepared at a concentration of 0.5 mg ml$^{-1}$ and containing 5 mg ml$^{-1}$ glucose to serve as respiratory substrate for the yeast cells, was added to the respirometer. The apparatus was tilted sideways to release air bubbles trapped in the dry baker's yeast and placed in a water bath preheated to 29° C. ComCat® a commercial bio-stimulant (EP 1 051 075), was used as a positive control at 0.5 mg/l (optimum concentration according to the manufacturers; Agraforum, Germany) and distilled water was used as a second control. Carbon dioxide released by the yeast cells was measured in cm$^3$ at 30 minute intervals over a three-hour incubation period by reading the released gas volume from the calibrated tube. Tests were performed in triplicate.
Method 2: the Effect of Different Organ Extracts on the Percentage Germination of Cress Seeds and Subsequent Seedling Growth.

Two sheets of special germination paper (30×30 cm) were used to test the effect of the crude organ extracts of *T. violacea* on the germination of Cress seeds as well as the subsequent seedling growth. A line, 10 cm from the top was drawn on the one sheet and 20 Cress seeds spaced evenly on the line. A second sheet of germination paper was placed on top of the first and moistened with either 0.5 mg ml$^{-1}$ solutions of the crude extracts, distilled water (negative control) or a 0.5 mg L$^{-1}$ solution of ComCat® (positive control). Both sheets of paper were rolled up longitudinally and placed upright in Erlenmeyr flasks containing either the aerial or below soil part crude extracts, distilled water or the ComCat® solution and kept at 25° C. in a growing chamber in the dark. Seed germination as well as coleoptile and root lengths were determined at 24 hours interval over a four-day incubation period. Tests were performed in triplicate.

Example 7

Cultivation of Pea (*Pisum sativum*) Plants

One hundred *Pisum sativum* cv. Mohanderfer seeds, obtained from a local seed merchant, were sown 2 cm from the surface in 20 pots at five seeds per pot using Bainsvlei soil and applying a standard NPK fertilizer mixture. The plants were allowed to grow for four weeks in a greenhouse while maintaining the soil at field capacity. After four weeks, two fully expanded leaflets of the same age were removed carefully from the fourth nodes of each plant and used for monitoring the potential of aerial part extracts of *T. violacea* to control *Ascochyta* blight in vivo.

Example 8

Isolation of *Mycosphaerella pinodes*

*Mycosphaerella pinodes* was isolated from diseased leaves and stems of various winter cultivars of field pea at the time of senescence. Collections of the infected plant material were made from the central and south eastern pea-growing areas of Ethiopia. Pieces of the diseased tissue were surface sterilized for 1 minute in 96% (v/v) ethanol, 3 minutes in a 3.5% (v/v) Sodium hypochloride solution (Moussart et al., 1998, European Journal of Plant Pathology 104:93-102.) and 30 seconds in 96% (v/v) ethanol. The tissues were subsequently aseptically transferred to corn meal agar amended with Streptomycin (0.3 ml/1) in 9 cm Petri dishes and incubated at 20±1° C. in a growth chamber. Isolates initially obtained from the plant material were then grown on Coon's medium (Ali et al., 1978, *Australian Journal of Agricultural Research* 29:841-849) consisting of 4 g maltose, 2 g $KNO_3$, 1.2 g $MgSO_4$, 2.7 g $KH_2PO_4$ and 20 g agar. Cultures were incubated for 14 days to obtain pycnidiospores. To obtain an isolate derived from a single uninucleate cell, a suspension of pycnidiospores was streaked on 15% water agar, incubated overnight at 20±1° C. and examined under a dissecting microscope (80×magnification). A germ tube from a pycnidiospore was severed and transferred to Coon's agar (Clulow & Lewis, 1992, Plant Pathology 41:362-369). Six isolates of *M. pinodes* were obtained. All isolates from a single-spore and cultures were maintained on Coon's agar slants and stored in the dark at 5° C.

Example 9

Preparation of a *M. Pinodes* Spore Suspension

Oat meal agar was prepared by gently heating 30 g of oats in 1 litre distilled water for one hour, stirring frequently, and subsequently filtering through a fine sieve upon which the volume was readjusted to one litre. Twenty grams of technical agar and 0.1 g Keltane AP was added to the filtrate to yield a 2% (m/v) agar concentration. The agar was autoclaved for 15 min, poured into Petri dishes and allowed to cool off before inoculation of three oatmeal plates with *M. pinodes* mycelia. Plates were incubated in a 12-hour photoperiod incubator at 20° C. for 14 days, to ensure the production of pycnidiospores. To prepare the inoculum (spore suspension), sterile distilled water was added to the 14-day old cultures dislodging spores gently with a sterile glass rod. The suspension was subsequently filtered through four layers of cheese cloth in order to remove the mycelia and the concentration of pycnidiospores was determined by means of a haemocytometer. The pycnidiospore concentration was adjusted to 1×10$^5$ spores per ml (Nasir & Hoppe, 1997, *Annals of Applied Biology* 18:32-33) with sterile distilled water prior to the inoculation of pea leaves.

Example 10

In Vivo Assessment of Crude Extract Phytotoxicity

Pea seeds were planted in plastic pots in Bainsvlei soil and grown in a glasshouse (minimum temperature 18° C.). Four weeks after planting, when the leaflets on the third and fourth nodes were fully expanded, three fourth node leaflets per replicate were removed from the plants, placed on Schleicher and Schull No. 595 filter paper and moistened with 4 ml of sterile distilled water in 9 cm Petri dishes. Thirty μl of each of a 0.25, 0.5, 1.0 and 2.0 mg/ml solution of the crude extract were placed separately on each of the three leaves per Petri dish and replicated three times. Treatment of the leaves with water and a standard fungicide (Carbendazim/difenoconazole) served as controls. Petri dishes containing the treated leaflets were incubated at 20° C. in a day/night incubator programmed for a 16-hour day cycle while 2 ml sterile distilled water was added daily to keep the filter paper moistened. Six days after treatment, phytotoxicity symptoms were assessed on leaves using a six-category scale [0=symptomless; 1=<5% necrotic flecks; 2=>5% necrotic flecks; 3=<50% of inoculated area necrotic; 4=50-100% of inoculated area necrotic; 5=necrosis spreading beyond inoculated areas] based on stereo microscopic observations (Clulow et al., 1991b, *Journal of Phytopathology* 131:322-332)].

Example 11

In Vivo Assessment of Crude Extract Antifungal Properties

Fourth node pea leaflets were obtained and sustained on moist filter paper in Petri dishes as described for the phytotoxicity assessment test. In vivo control of *M. pinodes* spore infection of the leaves by different concentrations (0.25, 0.5, 1.0 and 2.0 mg/ml) of the aerial part extract of *T. violacea* was followed in two ways namely, by inoculating the leaves with 15 µl of a spore suspension ($1 \times 10^5$ spores per ml; Nasir & Hoppe, 1997. l.c.) 30 minutes before applying the different concentrations of the crude extract separately, and the other way around. A standard fungicide, carbendazim/difenoconazole, currently used against *Ascochyta* blight in peas (Bretag et al., 1995, *Australian Journal of Experimental Agriculture* 35:525-530; Moussart et al., 1998, *European Journal of Plant Pathology* 104:93-102), as well as leaves inoculated only with the spore suspension, served as controls. Three leaves per Petri dish represented a replicate and the experiment was performed in triplicate. Petri dishes containing the differently treated leaves were incubated at 20° C., the optimal temperature for *M. pinodes* spore germination in a day/night incubator as illumination is necessary for spore germination (Roger & Tivoli, 1996, *Mycological Research* 100:304-306). After incubation for six days the foliar lesions were measured and leaf damage compared to that of the controls.

Example 12

Statistical Analysis of Data

Analysis of variance (ANOVA) was performed on the data, using the SAS statistical analysis program (SAS Institute Inc. 1999, SAS Institute software: Usage and reference. Version 6. SAS Institute). Duncan's LSD (least significant difference) procedure for comparison of means was applied to separate means ($P<0.05$). Treatments differing significantly were indicated in the tables by designating different sets of letters.

Example 13

Seed Treatment

Different lots of sorghum seeds were artificially inoculated separately with both covered (*Sporisorium sorghi*) and loose (*Sporisorium cruentum*) kernel smut spores at the rate of 5% (w/w) before application of seed treatments. An aerial crude extract of *T. violacea* was suspended in water at a rate of 2.0 g/l. Sorghum seed lots of 90 g each were treated with 15 ml of the crude extract by mixing thoroughly in a small plastic bag 24 h before planting. A standard synthetic seed dressing fungicide, Thiram (65 W), was applied in the same way at the rate of 0.25% (w/w) per kg seed and served as a positive control. Sorghum seeds were also artificially and separately inoculated with both loose and covered smuts spores, but were not treated with the extract or synthetic fungicide to serve as a second control.

Example 14

Field Trial

A field trial was conducted under irrigation at Melkassa Research Centre, Ethiopia in 2003. Plots were arranged in a randomised complete block design and treatments were replicated three times. Treated sorghum seeds were planted by hand in five rows, leaving 0.75 cm between rows, in 18.75 m² plots. Standard fertilizer was applied and plots were kept at field capacity by means of furrow irrigation. Disease incidence was recorded as percentage infected plants. Grain yield was determined on the whole plot.

Example 15

Activity Directed Liquid-Liquid Extraction

The following organic solvents, arranged in order of increasing polarity (dielectric constants) were used for semi-purification (liquid-liquid extraction) of the crude aerial and below soil part extracts separately: hexane (DC=2.0), diethyl ether (DC=4.3), ethyl acetate (DC=6.0), methylene chloride (DC=8.9). The extraction was done for both aerial and below soil parts. About 63.30 g of the methanol aerial part extract and 88.24 g of the below soil part extract were each dissolved in 50 ml distilled water and mixed with 50 ml hexane (1:1 ratio). Each mixture was shaken vigorously for 20 minutes on a mechanical shaker and subsequently transferred to a separating funnel allowing the two liquid phases to separate. The separated upper hexane layer was transferred into a beaker while the lower crude extract layer was again mixed with fresh 50 ml hexane and shaken as before. Fractionation was repeated 20 times with fresh solvent to optimize the recovery of compounds. The same procedure was followed with the other organic solvents. The four separated fractions were evaporated to dryness under vacuum in a water bath at 35° C. by means of a Büchi rotavapor.

The mass of recovered dry material was determined for each fraction. From the dried material of each fraction, 1 mg ml$^{-1}$ stock solutions in water were prepared. In order to establish the success of the fractionation process, a qualitative thin layer chromatography (TLC) profile was obtained for each fraction on a 0.5 mm Silica Gel 60 plate using chloroform:methanol:water (80:20:10) as mobile phase (Example 16). To determine where the active ingredients were located, the eight extracts were screened for antifungal properties. The same procedure was used as described in Example 5.

Example 16

Activity Directed Column Chromatography Fractionation (CCF)

Prior to column chromatography separation of active compounds in the semi-purified hexane extracts obtained by means of liquid-liquid extraction, using Silica Gel as stationary phase, the most effective solvent system was tested using Silica Gel TLC-plates. Solvent systems tested ranged from the least polar to the most polar and included: Hexane:Acetone (9.5:0.5-6:4); Hexane:Ethylacetate (8:2-6:4); Hexane:Acetone:Ethylacetate (6:2:2); Hexane:Acetone:Methanol (6:3:1) and Chloroform:Methanol (9:1-5:5). For both the aerial and below soil part extracts the most suitable solvent system was determined as Hexane:Acetone (9.5:0.5 and 9:1 respectively). An ordinary glass burette (1.5 m×2 cm) was used as a separating column. After placing a small piece of cotton wool at the bottom of the column a Silica Gel 60 slurry, previously prepared using the solvent system, was slowly poured into the column and allowed to settle until a final height of 1.49 m was reached. Care was taken to avoid air bubbles from forming. A separation funnel filled with about 1.5 litres of the solvent system was placed at the top of the column to ensure a continuous supply of the mobile phase and to maintain a 10 cm solvent column above the stationary phase. The column was equilibrated overnight before the bed volume was determined and the active semi-purified extract loaded onto the column. Twelve g of the dried active liquid-liquid extracts were dissolved in a suitable volume of the hexane:acetone solvent and gently loaded onto the column using a pipette. It was allowed to settle on the silica surface and to diffuse into the stationary phase before the mobile phase was allowed to migrate under gravitation.

Compounds were eluted at a flow rate of 0.5 ml/min and 12 ml fractions were collected using a fraction collector over a period of two to two and a half months. Columns were constantly monitored to ensure that they did not run dry. Fractions were collected until the columns were discoloured. Subsequently, the Hexane:Acetone (9.5:0.5) solvent system was replaced with a more polar Hexane:Acetone ratio of 9:1 or 8:2, 7:3, 6:4 or 5:5. Towards the end of the separation process more compounds were removed from the columns by means of 100% methanol.

Example 17

Qualitative Thin Layer Chromatography (Q-TLC)

Qualitative thin layer chromatography (TLC) was performed on 10×20 cm Kieselgel 60$F_{254}$, 0.25 mm, aluminium plates (Merck). Development of the TLC plates in the appropriate solvent was followed by spraying with formaldehyde (40%)-sulphuric acid (2:98) or with anisaldehyde-sulphuric acid-ethanol (5:5:90) and heated to 120° C. A total of about 3600 test-tubes were collected for each extract during the column chromatography separation outlined above. Qualitative thin layer chromatography (Q-TLC) was performed on the compounds separated in every third test-tube fraction collected. The same solvent system used for column chromatography separation was also used for TLC-separation. The plates were developed and subsequently investigated under UV-light at 254 and 365 nm. Visible fluorescent spots were marked with a pencil before the plates were sprayed with the vanillin-sulphuric acid reagent to show all the spots. RF-values of separate compounds as well as the TLC-profiles of the different column fractions were compared. Column fractions showing similar profiles and RF-values were combined. Combined column fractions were evaporated under reduced pressure at 40° C. in a rotary evaporator and the mass of the dried fractions determined.

Example 18

Determination of the Antifungal Activity of Combined Column Chromatography Fractions In order to ascertain in which column fractions most of the antifungal compounds were located, the same procedure as was outlined as described above, was followed using only *F. oxysporum*, relatively resistant to the aerial part extract as test organism. Only the most active combined column chromatography fractions were considered for further purification.

Example 19

Preparative Thin Layer Chromatography (P-TLC)

Only compounds in the most active combined column chromatography fractions were further purified by means of preparative thin layer chromatography (P-TLC). Separation was carried out on 20×20 cm glass plates coated with 1.0 mm Kieselgel $PF_{254}$ (Merck, Germany) which were air-dried and used without prior activation. Approximately 250-300 mg of each active combined column fraction was dissolved in a small volume (3-5 ml) of methanol, chloroform or the mobile phase, depending on the most effective solvent. The solution was streaked onto the baselines of about 20 P-TLC plates in thin uniform bands, applying small volumes at a time and drying between applications, until about 15 mg was applied per plate. In order to separate all compounds in a combined column fraction, in this case about 20-25 P-TLC plates were used. Hexane:Acetone (9.5:0.5) was used as solvent system to develop the plates in glass tanks. When the mobile phase reached the frontline, the plates were removed from the developing tanks and placed in a ventilated fume hood to dry. Subsequently, plates were examined under UV-light at 254 and 365 nm and the fluorescent bands marked with the sharp end of a spatula, before bands were scraped off using a spatula and transferred to corresponding labelled vials. Compounds were covered with a suitable volume of chloroform and eluted from the silica by vigorously shaking for 10 min before suction-filtering through a number of crucibles with labels corresponding to the labels of the silica bands. The filtrates were collected in corresponding pre-weighed flasks, placed in a ventilated fume cupboard to dry, the recovery mass determined and tested for antifungal activity.

Example 20

Determination of the Antifungal Activity of Compounds Purified by Means of Preparative Thin Layer Chromatography (P-TLC)

In order to ascertain which of the compounds separated by means of P-TLC were active, the same procedure as outlined in Example 5, was followed using *F. oxysporum* only as test organism. Only the most active compounds were purified further.

Example 21

Final Purification of Isolated Active Compounds

Only the most active isolated compounds were again tested for purity in an original analytical thin layer chromatography (TLC) system (Mikes and Chalmers, 1979, *Laboratory Handbook of Chromatographic and Allied Methods*. Ellis Horwood Ltd., London.) following the same Q-TLC (see section 6.2.3.3) and P-TLC (see above) procedures with slight modifications of the mobile phases. Either chloroform:methanol:water (80:20:10 v/v) or toluene:acetone:ethyl:acetate (7:2:1 v/v; Wagner and Bladt, 1996, *Plant Drug Analysis: A Thin Layer Chromatography Atlas, Second Edition*. Springer, New York) were used as solvent systems to separate active compounds from any other compounds that might have shared the same position on the Q-TLC or P-TLC plates. After drying the plates in a stream of air, compounds were either detected under UV-light at 254 and 365 nm or the plates were stained with 5% (v/v) ethanolic $H_2SO_4$ or 1% (m/v) Vanillin (1 g in 100 ml $H_2SO_4$; Wagner and Bladt, 1996). Non-pure compounds were again subjected to preparative TLC acidified with 1% (v/v) HCL until pure compounds were obtained. Only pure compounds that showed the highest antifungal activity were subjected to nuclear magnetic resonance (NMR) spectroscopy in order to identify them and to elucidate their molecular structures.

Example 22

NMR and Mass Spectroscopy

To identify the most bioactive compounds purified from the aerial and below soil plant parts and elucidate their molecular structures, isolated compounds were washed repeatedly with acetone to obtain an acceptable level of purity. Subsequently, the compounds were submitted to nuclear magnetic resonance spectroscopy ($^{13}C$ and $^1H$ 1D and 2D NMR). NMR-spectroscopy was performed on a Bruker ADVANCE 300 MHz DRX 300 spectrometer at 296K (23° C.) with tetramethylsilane (Si(CH3)$_4$; TMS) as the internal standard. The solvents used were deuteriochloroform (CDCl$_3$), or deuterioactetone [(CD$_3$)$_2$ CO] as indicated. Chemical shifts were reported in parts per million (ppm) on the δ-scale and coupling constants were given in Hz. MS spectra and mass determinations were obtained with a Kratos MS-80 mass spectrometer in the double focus electron impact (EI) mode.

The invention claimed is:

1. A method for inhibiting fungal infection of a crop in vivo under glasshouse or field conditions, the method comprising applying to said crop, before or after spore inoculation, in vivo under glasshouse or field conditions, an aqueous solution or suspension with a concentration of 0.2-2.0 g crude extract /l solution or suspension, wherein said solution or suspension is obtained from aerial parts of *Tulbaghia violacea* (wild garlic), wherein the applied solution or suspension inhibits fungal infection of the crop with an inhibition rate between 75 and 100%, wherein the solution or suspension comprises a compound 2,3,5,7,8-pentathiadecane, wherein the compound is an active antifungal compound and wherein said solution or suspension is obtained by the following steps:

(i) drying aerial parts of *Tulbaghia violacea* at 30-40° C.,
(ii) grinding the dried aerial parts to a grit size between 0.2 and 2 mm,
(iii) soaking the ground material in a polar organic solvent selected from the group consisting of methanol and ethanol, thus forming a suspension / solution;
(iv) performing a stirred extraction of the suspension and separating the supernatant from the solid phase;
(v) repeating step (iii) and (iv) at least one additional time,
(vi) combining the separated supernatants of step (iv) and (v), and removing the organic solvent by vacuum evaporation at 30-40° C., thus obtaining a crude extract residue, and
(vii) dissolving said crude extract in water to obtain the aqueous solution or suspension with a concentration of 0.2-2.0g crude extract /l solution or suspension.

2. The method of claim 1, wherein the crop is sorghum seeds before planting and the fungal infection is loose and covered kernel smuts.

3. The method of claim 2, wherein the concentration of the solution or suspension is 2.0 g crude extract/l solution or suspension.

4. The method of claim 1, wherein the solution or suspension further comprises solid pulverulent carrier materials or fillers.

5. The method of claim 1, wherein the drying in step (i) is carried out to the exclusion of sunlight.

6. The method of claim 1, wherein the solution or suspension is applied in a spray form.

7. The method of claim 1, wherein the solution or suspension is applied to the crop before spore inoculation with a concentration of 0.25g -1.0g crude extract / l solution or suspension and inhibits fungal infection of the crop with an inhibition rate between 80 and 100%.

8. The method of claim 1, wherein the solution or suspension is applied to the crop after spore inoculation with a concentration of 1.0g-2.0g crude extract /l solution or suspension and inhibits fungal infection of the crop with an inhibition rate between 80 and 100%.

9. The method of claim 2, wherein the solution or suspension has a concentration of 2.0g/l and prevents infection of covered kernel smuts by 100%.

10. The method of claim 2, wherein the treatment has no inhibitory effect on either seed germination or seedling growth.

* * * * *

UNITED STATES PATENT AND TRADEMARK OFFICE
CERTIFICATE OF CORRECTION

PATENT NO. : 8,697,149 B2  Page 1 of 1
APPLICATION NO. : 11/993132
DATED : April 15, 2014
INVENTOR(S) : Johannes Christiaan Pretorius It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1428 days.

Signed and Sealed this

Twenty-ninth Day of September, 2015

Michelle K. Lee
*Director of the United States Patent and Trademark Office*